US008686232B2

(12) United States Patent
Shen et al.

(10) Patent No.: US 8,686,232 B2
(45) Date of Patent: Apr. 1, 2014

(54) VIP3 TOXINS AND METHODS OF USE

(75) Inventors: Zhicheng Shen, Durham, NC (US); Gregory W. Warren, Apex, NC (US); Vance Kramer, Hillsborough, NC (US); Frank Shotkoski, Cary, NC (US)

(73) Assignee: Syngenta Participations AG, Basel (CH)

( * ) Notice: Subject to any disclaimer, the term of this patent is extended or adjusted under 35 U.S.C. 154(b) by 1073 days.

(21) Appl. No.: 12/106,847

(22) Filed: Apr. 21, 2008

(65) Prior Publication Data

US 2009/0328254 A1 Dec. 31, 2009

Related U.S. Application Data

(62) Division of application No. 10/505,315, filed as application No. PCT/US03/04735 on Feb. 20, 2003, now Pat. No. 7,378,493.

(60) Provisional application No. 60/362,250, filed on Mar. 6, 2002.

(51) Int. Cl.

| | |
|---|---|
| ***A01H 5/00*** | (2006.01) |
| ***A01H 5/10*** | (2006.01) |
| ***C12N 15/82*** | (2006.01) |
| ***C12N 15/32*** | (2006.01) |

(52) U.S. Cl.
USPC ..... 800/302; 536/23.71; 424/93.2; 435/320.1

(58) Field of Classification Search
None
See application file for complete search history.

(56) References Cited

U.S. PATENT DOCUMENTS

| | | | | |
|---|---|---|---|---|
| 5,625,136 | A | 4/1997 | Koziel et al. | |
| 5,877,012 | A | 3/1999 | Estruch et al. | 435/252.3 |
| 6,107,279 | A | 8/2000 | Estruch et al. | 514/12 |
| 6,137,033 | A | 10/2000 | Estruch et al. | 800/302 |
| 6,174,860 | B1 | 1/2001 | Kramer et al. | 514/12 |
| 6,291,156 | B1 | 9/2001 | Estruch et al. | 435/4 |
| 6,369,213 | B1 * | 4/2002 | Schnepf et al. | 536/23.71 |

FOREIGN PATENT DOCUMENTS

| | | | |
|---|---|---|---|
| WO | WO 97/46105 | 12/1997 | A01N 63/00 |
| WO | WO 98/00546 | 1/1998 | C12N 15/32 |
| WO | WO 98/18932 | 5/1998 | C12N 15/32 |
| WO | WO 98/44137 | 10/1998 | A01H 5/00 |
| WO | WO 99/33991 | 7/1999 | C12N 15/09 |
| WO | WO 99/57282 | 11/1999 | C12N 15/32 |
| WO | WO 02/078437 | 10/2002 | A01N 63/00 |

OTHER PUBLICATIONS

Selvapandiyan et al (2001, Appl. Environ. Microbiol. 67: 5855-5858).*
Lee et al (2003, Appl. Environ. Microbiol. 69:4648-4657).*
Guo et al (2004, Proc. Natl. Acad. Sci. USA 101: 9205-9210).*
Estruch, et al., 1996, Proceedings National Academy of Science, *Vip3, a novel Bacillus thuringiensis vegetative insecticidal protein with a wide spectrum of activities against lepidopteran insects*, 93: 5389-5394.
Selvapandiyan, A. et al., 2001, Applied and Environmental Microbiology, *The Bacillus thuringiensis Toxicity Analysis of N- and C-terminus-deleted Vegetative Insecticidal Protein From Bacillus thuringiensis*, 67 (12), 5855-5858 (2001).
Yu, et al., 1997, Applied and Environmental Microbiology, *The Bacillus thuringiensis Vegetative Insecticidal Protein Vip3 A Lyses Midgut Epithelium Cells of Susceptible Insects*, 63: 532-536.
Loguercio et al. First-tier screening for Vip-derived activities in tropical *Bacillus thuringiensis* strains by PCR and feeding bioassays: A critical assessment. GenBank Database [online], (Jul. 11, 2001), Accession No. AAK97481.
Loguercio et al. First-tier screening for Vip-derived activities in tropical *Bacillus thuringiensis* strains by PCR and feeding bioassays: A critical assessment. GenBank Database [online], (Jul. 11, 2001), Accession No. AAK97482.
Loguercio et al. First-tier screening for Vip-derived activities in tropical *Bacillus thuringiensis* strains by PCR and feeding bioassays: A critical assessment. GenBank Database [online], (Jul. 13, 2001), Accession No. AAK97484.
Loguercio et al. First-tier screening for Vip-derived activities in tropical *Bacillus thuringiensis* strains by PCR and feeding bioassays: A critical assessment. GenBank Database [online], (Jul. 13, 2001), Accession No. AAK97485.
Loguercio et al. First-tier screening for Vip-derived activities in tropical *Bacillus thuringiensis* strains by PCR and feeding bioassays: A critical assessment. GenBank Database [online], (Jul. 14, 2001), Accession No. AAK97486.
Loguercio et al. First-tier screening for Vip-derived activities in tropical *Bacillus thuringiensis* strains by PCR and feeding bioassays: A critical assessment. GenBank Database [online], (Jul. 11, 2001), Accession No. AAK97487.
Doss et al. Cloning and expression of the vegetative insecticidal protein (vip3V) gene of *Bacillus thuringiensis* in *Escherichia coli*. GenBank Database [online], (Apr. 23, 2001, Accession No. AF373030.
Cai et al. Vegetative insecticidal protein gene vip83 from *Bacillus thuringiensis* servar leesis strain YBT-833. GenBank Database [online], (Jul. 08, 2001), Accession No. AY044227.
Yu et al. Cloning and expression of Vip3A gene from *Bacillus thuringiensis* strain S10-1. GenBank Database [online], (Jan. 17, 2002), Accession No. AY074706.
Chen et al. Cloning and expression of Vip3A gene from *Bacillus thuringiensis* strain S10-1. GenBank Database [online], (Jan. 17, 2002), Accession No. AY074707.
Chen et al. Cloning and expression of Vip3A gene from *Bacillus thuringiensis* strain S10-1. GenBank Database [online], (Jan. 17, 2002), Accession No. AY074708.
Murray, E.E. et al. Codon usage in plant genes. Nucleic Acids Research. (1989), p. 477-498, 17(2).

* cited by examiner

*Primary Examiner* — Anne Kubelik
(74) *Attorney, Agent, or Firm* — Karen Magri

(57) ABSTRACT

Nucleic acid molecules encoding novel Vip3 toxins that are highly active against a wide range of lepidopteran insect pests are disclosed. The nucleic acid molecules can be used to transform various prokaryotic and eukaryotic organisms to express the Vip3 toxins. These recombinant organisms can be used to control lepidopteran insects in various environments.

29 Claims, No Drawings

SEQUENCE LISTING

```
<160> NUMBER OF SEQ ID NOS: 33

<210> SEQ ID NO 1
<211> LENGTH: 2367
<212> TYPE: DNA
<213> ORGANISM: Bacillus thuringiensis
<220> FEATURE:
<221> NAME/KEY: misc_feature
<222> LOCATION: (1)..(2367)
<223> OTHER INFORMATION: Native vip3C coding sequence.
      An "r" at position 2213 represents the nucleotide g or a.

<400> SEQUENCE: 1

atgaacaaga ataatactaa attaagcaca agagccctac cgagttttat tgattatttt      60

aatggcattt atggatttgc cactggtatc aaagacatta tgaatatgat ttttaaaacg     120

gatacaggtg gtaatctaac cttagacgaa atcctaaaga atcagcagtt actaaatgag     180

atttctggta aattggatgg ggtaaatggg agcttaaatg atcttatcgc acagggaaac     240

ttaaatacag aattatctaa ggaaatctta aaaatcgcaa atgaacagaa tcaagtctta     300

aatgatgtta ataacaaact cgatgcgata aatacgatgc ttcatatata tctacctaaa     360

attacatcta tgttaagtga tgtaatgaag caaaattatg cgctaagtct gcaaatagaa     420

tacttaagta agcaattgca agaaatttct gataaattag atattattaa cgtaaatgtt     480

cttattaact ctacacttac tgaaattaca cctgcatatc aacggattaa atatgtgaat     540

gaaaaatttg aagaattaac ttttgctaca gaaaccactt taaaagtaaa aaaggatagc     600

tcgcctgctg atattcttga tgagttaact gaattaactg aactagcgaa aagtgttaca     660
```

```
aaaaatgacg ttgatggttt tgaattttac cttaatacat tccacgatgt aatggtagga    720

aataatttat tcgggcgttc agctttaaaa actgcttcag aattaattgc taaagaaaat    780

gtgaaaacaa gtggcagtga agtaggaaat gtttataatt tcttaattgt attaacagct    840

ctacaagcaa aagcttttct tactttaaca acatgccgaa aattattagg cttagcaggt    900

attgattata cttctattat gaatgaacat ttaaataagg aaaaagagga atttagagta    960

aacatccttc ctacactttc taatactttt tctaatccta attatgcaaa agttaaagga   1020

agtgatgaag atgcaaagat gattgtggaa gctaaaccag gacatgcatt ggttgggttt   1080

gaaatgagca atgattcaat cacagtatta aaagtatatg aggctaagct aaaacaaaat   1140

tatcaagttg ataaggattc cctatcggag gttatttatg gtgatacgga taaattattt   1200

tgtccagatc aatctgaaca aatatattat acaaataaca tagtattccc aaatgaatat   1260

gtaattacta aaattgattt cactaaaaaa atgaaaactt taagatatga ggtaacagcg   1320

aatttttatg attcttctac aggagaaatt gacttaaata agaaaaaagt agaatcaagt   1380

gaagcggagt atagaacgtt aagtgctaat gatgatggag tgtatatgcc attaggtgtc   1440

atcagtgaaa catttttgac tccgataaat gggtttggcc tccaagctga tgaaaattca   1500

agattaatta ctttaacatg taaatcatat ttaagagaac tactgctagc aacagactta   1560

agcaataaag aaactaaatt gatcgtccca ccaagtggtt ttattagcaa tattgtagag   1620

aacgggtcca tagaagagga caatttagag ccgtggaaag caaataataa gaatgcgtat   1680

gtagatcata caggcggagt gaatggaact aaagctttat atgttcataa ggacggagga   1740

ttttcacaat ttattggaga taagttaaaa ccgaaaactg agtatgtaat ccaatatact   1800

gttaaaggaa aaccttctat tcatttaaaa gatgaaaata ctggatatat tcattatgaa   1860

gatacaaata ataatttaaa agattatcaa actattacta aacgttttac tacaggaact   1920

gatttaaagg gagtgtattt aattttaaaa agtcaaaatg gagatgaagc ttggggagat   1980

aaatttacaa ttttagaaat taagcctgcg gaggatttat taagcccaga attaattaat   2040

ccgaattctt ggattacgac tccaggggct agcatttcag gaaataaact tttcattaac   2100

ttggggacaa atgggacctt tagacaaagt ctttcattaa acagttattc aacttatagt   2160

ataagcttta ctgcatcagg accatttaat gtgacggtaa gaaattctag ggragtatta   2220

tttgaacgaa gcaaccttat gtcttcaact agtcatattt ctgggacatt caaaactgaa   2280

tccaataata ccggattata tgtagaactt tcccgtcgct ctggtggtgg tggtcatata   2340

tcatttgaaa acgtttctat taaataa                                       2367
```

```
<210> SEQ ID NO 2
<211> LENGTH: 788
<212> TYPE: PRT
<213> ORGANISM: Bacilus thuringiensis
<220> FEATURE:
<221> NAME/KEY: MISC_FEATURE
<222> LOCATION: (1)..(788)
<223> OTHER INFORMATION: Vip3C Toxin
      The Xaa at position 738 is either the amino acid Glu or Gly.

<400> SEQUENCE: 2

Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45
```

```
Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Gly Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Val Gly Phe Glu Met Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Thr Asp Lys Leu Phe
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Lys Val Glu Ser Ser Glu Ala Glu Tyr
    450                 455                 460

Arg Thr Leu Ser Ala Asn Asp Asp Gly Val Tyr Met Pro Leu Gly Val
```

```
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Ser Ile
    530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Phe Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
    610                 615                 620

Asn Leu Lys Asp Tyr Gln Thr Ile Thr Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Lys Phe Thr Ile Leu Glu Ile Lys Pro Ala Glu Asp
            660                 665                 670

Leu Leu Ser Pro Glu Leu Ile Asn Pro Asn Ser Trp Ile Thr Thr Pro
        675                 680                 685

Gly Ala Ser Ile Ser Gly Asn Lys Leu Phe Ile Asn Leu Gly Thr Asn
    690                 695                 700

Gly Thr Phe Arg Gln Ser Leu Ser Leu Asn Ser Tyr Ser Thr Tyr Ser
705                 710                 715                 720

Ile Ser Phe Thr Ala Ser Gly Pro Phe Asn Val Thr Val Arg Asn Ser
                725                 730                 735

Arg Xaa Val Leu Phe Glu Arg Ser Asn Leu Met Ser Ser Thr Ser His
            740                 745                 750

Ile Ser Gly Thr Phe Lys Thr Glu Ser Asn Asn Thr Gly Leu Tyr Val
        755                 760                 765

Glu Leu Ser Arg Arg Ser Gly Gly Gly Gly His Ile Ser Phe Glu Asn
    770                 775                 780

Val Ser Ile Lys
785


<210> SEQ ID NO 3
<211> LENGTH: 2367
<212> TYPE: DNA
<213> ORGANISM: Artificial Sequence
<220> FEATURE:
<223> OTHER INFORMATION: Maize optimized vip3C coding sequence.
      An "r" at positions 2213 and 2214 represents the nucleotide g or
      a.

<400> SEQUENCE: 3

atgaacaaga acaacaccaa gctctccacc cgcgccctcc cgtccttcat cgactacttc      60

aacggcatct acggcttcgc caccggcatc aaggacatca tgaacatgat cttcaagacc     120

gacaccggcg gcaacctcac cctcgacgag atcctcaaga accagcagct cctcaacgag     180
```

-continued

```
atcagcggca agctcgacgg cgtgaacggc tccctcaacg acctcatcgc ccagggcaac    240
ctcaacaccg agctgtccaa ggagatcctc aagatcgcca acgagcagaa ccaggtgctc    300
aacgacgtga acaacaagct cgacgccatc aacaccatgc tccacatcta cctcccgaag    360
atcacctcca tgctctccga cgtgatgaag cagaactacg ccctctccct ccagatcgag    420
tacctctcca agcagctcca ggagatcagc gacaagctcg acatcatcaa cgtgaacgtg    480
ctcatcaact ccaccctcac cgagatcacc ccggcctacc agcgcatcaa gtacgtgaac    540
gagaagttcg aggagctgac cttcgccacc gagaccaccc tcaaggtgaa gaaggactcc    600
tccccggccg acatcctcga cgagctgacc gagctgaccg agctggccaa gtccgtgacc    660
aagaacgacg tggacggctt cgagttctac ctcaacacct tccacgacgt gatggtgggc    720
aacaacctct tcggccgctc cgccctcaag accgcctccg agctgatcgc caaggagaac    780
gtgaagacct ccggctccga ggtgggcaac gtgtacaact tcctcatcgt gctcaccgcc    840
ctgcaggcca aggccttcct caccctcacc acctgccgca agctcctcgg cctcgccggc    900
atcgactaca cctccatcat gaacgagcac ctcaacaagg agaaggagga gttccgcgtg    960
aacatcctcc cgaccctctc caacaccttc tccaacccga actacgccaa ggtgaagggc   1020
tccgacgagg acgccaagat gatcgtggag gccaagccgg gccacgccct cgtgggcttc   1080
gagatgtcca acgactccat caccgtgctc aaggtgtacg aggccaagct caagcagaac   1140
taccaggtgg acaaggactc cctctccgag gtgatctacg gcgacaccga caagctcttc   1200
tgcccggacc agtccgagca gatatactac accaacaaca tcgtgttccc gaacgagtac   1260
gtgatcacca agatcgactt caccaagaag atgaagaccc tccgctacga ggtgaccgcc   1320
aacttctacg actcctccac cggcgagatc gacctcaaca agaagaaggt ggagtcctcc   1380
gaggccgagt accgcaccct ctccgccaac gacgacggcg tgtacatgcc gctcggcgtg   1440
atctccgaaa ccttcctcac cccgatcaac ggcttcggcc tccaggccga cgagaactcc   1500
cgcctcatca ccctcacctg caagtcctac ctccgcgagc tgctcctcgc caccgacctc   1560
tccaacaagg agaccaagct catcgtgccg ccgtccggct tcatctccaa catcgtggag   1620
aacggctcca tcgaggagga caacctcgag ccgtggaagg ccaacaacaa gaacgcctac   1680
gtggaccaca ccggcggcgt gaacggcacc aaggccctct acgtgcacaa ggacggcggc   1740
ttctcccagt tcatcggcga caagctcaag ccgaagaccg agtacgtgat ccagtacacc   1800
gtgaagggca agccgtccat ccacctcaag gacgagaaca ccggctacat ccactacgag   1860
gacaccaaca acaacctcaa ggactaccag accatcacca agcgcttcac caccggcacc   1920
gacctcaagg gcgtgtacct catcctcaag tcccagaacg gcgacgaggc ctggggcgac   1980
aagttcacca tccttgagat caagccggcc gaggacctcc tctccccgga gctgatcaac   2040
ccgaactcct ggatcaccac cccgggcgcc tccatctccg gcaacaagct cttcatcaac   2100
ctcggcacca acggcacctt ccgccagtcc ctctccctca actcctactc cacctactcc   2160
atctccttca ccgcctccgg cccgttcaac gtgaccgtgc gcaactcccg cgrrgtgctc   2220
ttcgagcgct ccaacctcat gtcctccacc tcccacatct ccggcacctt caagaccgag   2280
tccaacaaca ccggcctcta cgtggagctg tcccgccgct ccggcggcgg cggccacatc   2340
tccttcgaga acgtgtccat caagtag                                       2367
```

<210> SEQ ID NO 4
<211> LENGTH: 2370
<212> TYPE: DNA
<213> ORGANISM: Bacillus thuringiensis
<220> FEATURE:

<221> NAME/KEY: misc_feature
<222> LOCATION: (1)..(2370)
<223> OTHER INFORMATION: vip3A(a) native coding sequence.

<400> SEQUENCE: 4

```
atgaacaaga ataatactaa attaagcaca agagccttac caagttttat tgattatttt     60
aatggcattt atggatttgc cactggtatc aaagacatta tgaacatgat tttaaaaacg    120
gatacaggtg gtgatctaac cctagacgaa attttaaaga atcagcagtt actaaatgat    180
atttctggta aattggatgg ggtgaatgga agcttaaatg atcttatcgc acagggaaac    240
ttaaatacag aattatctaa ggaaatatta aaaattgcaa atgaacaaaa tcaagtttta    300
aatgatgtta ataacaaact cgatgcgata aatacgatgc ttcgggtata tctacctaaa    360
attacctcta tgttgagtga tgtaatgaaa caaaattatg cgctaagtct gcaaatagaa    420
tacttaagta aacaattgca agagatttct gataagttgg atattattaa tgtaaatgta    480
cttattaact ctacacttac tgaaattaca cctgcgtatc aaaggattaa atatgtgaac    540
gaaaaatttg aggaattaac ttttgctaca gaaactagtt caaaagtaaa aaaggatggc    600
tctcctgcag atattcttga tgagttaact gagttaactg aactagcgaa aagtgtaaca    660
aaaaatgatg tggatggttt tgaattttac cttaatacat tccacgatgt aatggtagga    720
aataatttat tcgggcgttc agctttaaaa actgcatcgg aattaattac taaagaaaat    780
gtgaaaacaa gtggcagtga ggtcggaaat gtttataact tcttaattgt attaacagct    840
ctgcaagcaa aagcttttct tactttaaca acatgccgaa aattattagg cttagcagat    900
attgattata cttctattat gaatgaacat ttaaataagg aaaaagagga atttagagta    960
aacatcctcc ctacactttc taatactttt tctaatccta attatgcaaa agttaaagga   1020
agtgatgaag atgcaaagat gattgtggaa gctaaaccag gacatgcatt gattgggttt   1080
gaaattagta atgattcaat tacagtatta aaagtatatg aggctaagct aaaacaaaat   1140
tatcaagtcg ataaggattc cttatcggaa gttatttatg gtgatatgga taaattattg   1200
tgcccagatc aatctgaaca aatctattat acaaataaca tagtatttcc aaatgaatat   1260
gtaattacta aaattgattt cactaaaaaa atgaaaactt taagatatga ggtaacagcg   1320
aatttttatg attcttctac aggagaaatt gacttaaata agaaaaaagt agaatcaagt   1380
gaagcggagt atagaacgtt aagtgctaat gatgatgggg tgtatatgcc gttaggtgtc   1440
atcagtgaaa catttttgac tccgattaat gggtttggcc tccaagctga tgaaaattca   1500
agattaatta ctttaacatg taaatcatat ttaagagaac tactgctagc aacagactta   1560
agcaataaag aaactaaatt gatcgtcccg ccaagtggtt ttattagcaa tattgtagag   1620
aacgggtcca tagaagagga caatttagag ccgtggaaag caaataataa gaatgcgtat   1680
gtagatcata caggcggagt gaatggaact aaagctttat atgttcataa ggacggagga   1740
atttcacaat ttattggaga taagttaaaa ccgaaaactg agtatgtaat ccaatatact   1800
gttaaaggaa aaccttctat tcatttaaaa gatgaaaata ctggatatat tcattatgaa   1860
gatacaaata ataatttaga agattatcaa actattaata aacgttttac tacaggaact   1920
gatttaaagg gagtgtattt aattttaaaa agtcaaaatg gagatgaagc ttggggagat   1980
aactttatta ttttggaaat tagtccttct gaaaagttat taagtccaga attaattaat   2040
acaaataatt ggacgagtac gggatcaact aatattagcg gtaatacact cactctttat   2100
cagggaggac gagggattct aaaacaaaac cttcaattag atagtttttc aacttataga   2160
gtgtattttt ctgtgtccgg agatgctaat gtaaggatta gaaattctag ggaagtgtta   2220
```

```
tttgaaaaaa gatatatgag cggtgctaaa gatgtttctg aaatgttcac tacaaaattt   2280

gagaaagata acttttatat agagctttct caagggaata atttatatgg tggtcctatt   2340

gtacattttt acgatgtctc tattaagtaa                                    2370


<210> SEQ ID NO 5
<211> LENGTH: 789
<212> TYPE: PRT
<213> ORGANISM: Bacillus thuringiensis
<220> FEATURE:
<221> NAME/KEY: MISC_FEATURE
<222> LOCATION: (1)..(789)
<223> OTHER INFORMATION: Vip3A toxin

<400> SEQUENCE: 5

Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335
```

```
Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Ser Ile
    530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
    610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
            660                 665                 670

Leu Leu Ser Pro Glu Leu Ile Asn Thr Asn Asn Trp Thr Ser Thr Gly
        675                 680                 685

Ser Thr Asn Ile Ser Gly Asn Thr Leu Thr Leu Tyr Gln Gly Gly Arg
    690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
            740                 745                 750

Ser Glu Met Phe Thr Thr Lys Phe Glu Lys Asp Asn Phe Tyr Ile Glu
```

```
        755                 760                 765

Leu Ser Gln Gly Asn Asn Leu Tyr Gly Gly Pro Ile Val His Phe Tyr
    770                 775                 780

Asp Val Ser Ile Lys
785


<210> SEQ ID NO 6
<211> LENGTH: 2364
<212> TYPE: DNA
<213> ORGANISM: Bacillus thuringiensis
<220> FEATURE:
<221> NAME/KEY: misc_feature
<222> LOCATION: (1)..(2364)
<223> OTHER INFORMATION: vip3B native coding sequence.

<400> SEQUENCE: 6

atgaacaaga ataatactaa attaaacgca agggccttac cgagttttat tgattatttt      60

aatggcattt atggatttgc cactggtatc aaagacatta tgaacatgat tttaaaaacg     120

gatacaggtg gaaatctaac cctagacgaa attttaaaaa atcagcagtt attaaatgag     180

atttctggta aattggatgg ggtaaatggg agcttaaacg atcttatcgc acagggaaac     240

ttaaatacag aattatctaa ggaaatctta aaaattgcaa atgagcagaa tcaagtctta     300

aatgatgtta ataacaaact taatgcgata aatacaatgc ttcacatata tctacctaaa     360

attacatcta tgttaaatga tgtaatgaaa caaaattatg cactaagtct gcaaatagaa     420

tacctaagta aacaattgca agaaatttcc gacaagttag atgtcattaa cgtgaatgta     480

cttattaact ctacacttac tgaaattaca cctgcgtatc aacggatgaa atatgtaaat     540

gaaaaatttg aagatttaac ttttgctaca gaaaccactt taaaagtaaa aaagaatagc     600

tcccctgcag atattcttga tgagttaact gagttaactg aactagcgaa aagtgtaaca     660

aaaaatgacg tggatggttt tgaattttac cttaatacat tccacgatgt aatggtagga     720

aacaatttat tcgggcgttc agctttaaaa actgcttcgg aattaatcgc taaagaaaat     780

gtgaaaacaa gtggcagtga ggtaggaaat gtttataatt tcttaattgt attaacagct     840

ctgcaagcaa aagcttttct tactttaaca acatgccgga aattattagg cttagcagat     900

attgattata ctttcattat gaatgaacat ttagataagg aaaaagagga atttagagta     960

aatatccttc ctacactttc taatactttt tctaatccta actatgcaaa agctaaagga    1020

agcaatgaag atgcaaagat aattgtggaa gctaaaccag gatatgcttt ggttggattt    1080

gaaatgagca atgattcaat cacagtatta aaagcatatc aggctaagct aaaacaagat    1140

tatcaagttg ataaagattc gttatcagaa attgtctatg gtgatatgga taaattattg    1200

tgcccggatc aatctgaaca aatatattat acaaataaca ttgcttttcc caatgaatat    1260

gtaattacta aaattacttt tactaaaaaa atgaatagtt taagatatga ggcaacagct    1320

aatttttatg attcttctac aggggatatt gatctaaata agacaaaagt agaatcaagt    1380

gaagcagagt atagtacgct aagtgctagt actgatggag tctatatgcc gttaggtatt    1440

atcagtgaaa catttttgac tccaattaat gggtttggaa tcgtagtcga tgaaaattca    1500

aaattagtaa atttaacatg taaatcatat ttaagagagg tattattagc aacagactta    1560

agtaataaag aaactaaatt gattgtccca cctattggtt ttattagcaa tattgtagaa    1620

aatgggaact tagagggaga aaacttagag ccgtggaaag caaataacaa aaatgcgtat    1680

gtagatcata caggcggcgt aaatggaact aaagctttat atgttcataa ggatggtgag    1740

ttttcacaat ttattggaga taagttgaaa tcgaaaacag aatatgtaat tcaatatatt    1800
```

```
gtaaagggaa aagcttctat tcttttgaaa gatgaaaaaa atggtgattg catttatgaa   1860

gatacaaata atggtttaga agattttcaa accattacta aaagttttat tacaggaacg   1920

gattcttcag gagttcattt aatatttaat agtcaaaatg gcgatgaagc atttggggaa   1980

aactttacta tttcagaaat taggctttcc gaagatttat taagtccaga attgataaat   2040

tcagatgctt gggttggatc tcagggaact tggatctcag gaaattcact cactattaat   2100

agtaatgtga atggaacttt tcgacaaaac ctttcgttag aaagctattc aacttatagt   2160

atgaacttta atgtgaatgg atttgccaag gtgacagtaa gaaattcccg tgaagtatta   2220

tttgaaaaaa attatccgca gctttcacct aaagatattt ctgaaaaatt cacaactgca   2280

gccaataata ccgggttgta tgtagagctt tctcgtttta catcgggtgg cgctataaat   2340

ttccggaatt tttcgattaa gtga                                          2364
```

<210> SEQ ID NO 7
<211> LENGTH: 787
<212> TYPE: PRT
<213> ORGANISM: Bacillus thuringiensis
<220> FEATURE:
<221> NAME/KEY: MISC_FEATURE
<222> LOCATION: (1)..(787)
<223> OTHER INFORMATION: Vip3B Toxin

<400> SEQUENCE: 7

```
Met Asn Lys Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asn Ala Ile Asn Thr
            100                 105                 110

Met Leu His Ile Tyr Leu Pro Lys Ile Thr Ser Met Leu Asn Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Val Ile Asn Val Asn Val
145                 150                 155                 160

Leu Ile Asn Ser Thr Leu Thr Glu Ile Thr Pro Ala Tyr Gln Arg Met
                165                 170                 175

Lys Tyr Val Asn Glu Lys Phe Glu Asp Leu Thr Phe Ala Thr Glu Thr
            180                 185                 190

Thr Leu Lys Val Lys Lys Asn Ser Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255
```

```
Ala Lys Glu Asn Val Lys Thr Ser Gly Ser Glu Val Gly Asn Val Tyr
        260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Phe Ile Met Asn Glu His Leu Asp Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Ala Lys Gly Ser Asn Glu Asp Ala Lys Ile Ile Val Glu Ala Lys
            340                 345                 350

Pro Gly Tyr Ala Leu Val Gly Phe Glu Met Ser Asn Asp Ser Ile Thr
        355                 360                 365

Val Leu Lys Ala Tyr Gln Ala Lys Leu Lys Gln Asp Tyr Gln Val Asp
    370                 375                 380

Lys Asp Ser Leu Ser Glu Ile Val Tyr Gly Asp Met Asp Lys Leu Leu
385                 390                 395                 400

Cys Pro Asp Gln Ser Glu Gln Ile Tyr Tyr Thr Asn Asn Ile Ala Phe
                405                 410                 415

Pro Asn Glu Tyr Val Ile Thr Lys Ile Thr Phe Thr Lys Lys Met Asn
            420                 425                 430

Ser Leu Arg Tyr Glu Ala Thr Ala Asn Phe Tyr Asp Ser Ser Thr Gly
        435                 440                 445

Asp Ile Asp Leu Asn Lys Thr Lys Val Glu Ser Ser Glu Ala Glu Tyr
    450                 455                 460

Ser Thr Leu Ser Ala Ser Thr Asp Gly Val Tyr Met Pro Leu Gly Ile
465                 470                 475                 480

Ile Ser Glu Thr Phe Leu Thr Pro Ile Asn Gly Phe Gly Ile Val Val
                485                 490                 495

Asp Glu Asn Ser Lys Leu Val Asn Leu Thr Cys Lys Ser Tyr Leu Arg
            500                 505                 510

Glu Val Leu Leu Ala Thr Asp Leu Ser Asn Lys Glu Thr Lys Leu Ile
        515                 520                 525

Val Pro Pro Ile Gly Phe Ile Ser Asn Ile Val Glu Asn Gly Asn Leu
    530                 535                 540

Glu Gly Glu Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Glu Phe Ser Gln Phe Ile Gly Asp Lys Leu Lys Ser Lys
            580                 585                 590

Thr Glu Tyr Val Ile Gln Tyr Ile Val Lys Gly Lys Ala Ser Ile Leu
        595                 600                 605

Leu Lys Asp Glu Lys Asn Gly Asp Cys Ile Tyr Glu Asp Thr Asn Asn
    610                 615                 620

Gly Leu Glu Asp Phe Gln Thr Ile Thr Lys Ser Phe Ile Thr Gly Thr
625                 630                 635                 640

Asp Ser Ser Gly Val His Leu Ile Phe Asn Ser Gln Asn Gly Asp Glu
                645                 650                 655

Ala Phe Gly Glu Asn Phe Thr Ile Ser Glu Ile Arg Leu Ser Glu Asp
            660                 665                 670

Leu Leu Ser Pro Glu Leu Ile Asn Ser Asp Ala Trp Val Gly Ser Gln
        675                 680                 685
```

```
Gly Thr Trp Ile Ser Gly Asn Ser Leu Thr Ile Asn Ser Asn Val Asn
    690                 695                 700

Gly Thr Phe Arg Gln Asn Leu Ser Leu Glu Ser Tyr Ser Thr Tyr Ser
705                 710                 715                 720

Met Asn Phe Asn Val Asn Gly Phe Ala Lys Val Thr Val Arg Asn Ser
                725                 730                 735

Arg Glu Val Leu Phe Glu Lys Asn Tyr Pro Gln Leu Ser Pro Lys Asp
            740                 745                 750

Ile Ser Glu Lys Phe Thr Thr Ala Ala Asn Asn Thr Gly Leu Tyr Val
        755                 760                 765

Glu Leu Ser Arg Phe Thr Ser Gly Gly Ala Ile Asn Phe Arg Asn Phe
    770                 775                 780

Ser Ile Lys
785


<210> SEQ ID NO 8
<211> LENGTH: 2407
<212> TYPE: DNA
<213> ORGANISM: Bacillus thuringiensis
<220> FEATURE:
<221> NAME/KEY: misc_feature
<222> LOCATION: (1)..(2406)
<223> OTHER INFORMATION: vip3Z native coding sequence.

<400> SEQUENCE: 8

atgaataata ctaagttaaa cgcaagggct ttaccaagtt ttattgatta ttttaatggc      60

atttatggat ttgccactgg tatcaaagac attatgaaca tgatttttaa aacggataca     120

ggtggtggta atttaacact agatgaaatt ttaaagaatc aagatttatt aaatcaaatc     180

tcagataaac tcgatggaat taatggagat ttaggtgatc ttattgcaca aggcaattta     240

aattcagaac taactaagga attattaaaa attgcgaatg agcagaatct gatgttaaat     300

aatgttaatg ctcaacttaa ttcaataaat tcaacactta acacctatct gccaaaaatt     360

acatctatgc taagtgaggt aatgaaacaa aactatgtat taagtctaca aatagaattt     420

cttagtgaac aattacaaga aatatcagat aaacttgatg ttatcaattt aaatgtatta     480

attaactcta cattgacaga aattacgcct gcatatcaac gtattaaata tgtaaatgat     540

aaatttgatg aattgacttc tactgtggaa aaaaatccga aaattaatca agataatttt     600

actgaagatg ttattgataa tttaactgat ttaactgaac tagcacgaag tgtaacgaga     660

aatgatatgg atagttttga attttatatt aaaactttcc atgatgtgat gataggaaat     720

aatttattca gtcgttctgc attaaaaact gcttcagaat taattgctaa ggaaaatata     780

catactatgg gaagtgaaat tggtaatgtc tacactttta tggttgtttt gacttcctta     840

caagcaaaag cgttcctaac tttaactgca tgccgtaaat tattaggatt aacagatatc     900

gattatacac aaattatgaa tgaaaattta aatagagaaa aagaggaatt tcgcttaaat     960

attcttccta cactttctaa tgatttttct aatcctaatt atacagaaac tttaggaagt    1020

gatcttgtag atcctattgt tacgttagaa gctgatcctg gttatgcttt aataggtttt    1080

gagattctca atgatccact tccagtatta aaagtatatc aggcaaagct aaaaccaaat    1140

tatcaagtcg acaaagagtc gattatggaa aatatttatg gaaatatcca caaactactt    1200

tgtccaaaac aacgtcacca aaaatattat ataaaagaca ttacatttcc tgaaggttat    1260

gtaatcacca aaattgtttt tgaaaaaaaa ttgaatctat taggatatga agtaacagca    1320

aatctttatg acccatttac aggaagtatc gatttgaata agactattct agaatcatgg    1380
```

```
aaggaagaat gctgtgaaga agaatgctgt gaagaagaat gctgtgaaga agaatgctgt   1440

gaagaattat ataaaattat agaggcggat actaacggtg tttatatgcc gttgggagta   1500

attagtgaaa catttttaac accaatctat agttttaaac taattattga cgaaagaaca   1560

aagagaatat ctttagcggg taaatcttat ttacgtgaat ctttactagc cacagattta   1620

gttaataaag atacgaattt aattccttca cccaatggtt tcattaacag tattgtggaa   1680

aattggaata taacatcgga taatatagag ccctggaaag cgaataataa aaatgcatat   1740

gtcgataaga cggatgacat ggtgggattt aactctttat atactcataa ggatggggaa   1800

ttcttgcaat ttattggagc taagttaaag gctaaaactg agtatatcat tcaatatact   1860

gtaaaaggga gtccggaagt ttatttgaaa aacaataaag gtatctttta tgaggataca   1920

acaaataaat ttgatacgtt tcaaactata actaaaaagt tcaattcagg agtagatcca   1980

tccgaaatat atctagtttt taaaaatcaa attggatatg aagcatgggg aaataaattt   2040

attatactag aaatcaagtc atttgaaacc ctaccacaaa tattaaaacc tgaaaattgg   2100

atgccttttg gtaatgctga gattaaagaa gatggaaaaa ttgagatttc aggtaatgga   2160

actatgacgc aaaatattca attagaacag aattccaagt atcatctaag attttctgta   2220

aaaggaaaag ggagagtagc gatacaaact caaagctccc atataaatgt accagctaca   2280

aacgaagagg tttctacaat gattacaact agaaacttat acggtgaagg tatgatatac   2340

ctatttaatg atgacgtgga gaactccaaa gttatttttt cggatgtatc tctagttaaa   2400

gaatagg                                                             2407
```

<210> SEQ ID NO 9
<211> LENGTH: 801
<212> TYPE: PRT
<213> ORGANISM: Bacillus thuringiensis
<220> FEATURE:
<221> NAME/KEY: MISC_FEATURE
<222> LOCATION: (1)..(801)
<223> OTHER INFORMATION: Vip3Z toxin

<400> SEQUENCE: 9

```
Met Asn Asn Thr Lys Leu Asn Ala Arg Ala Leu Pro Ser Phe Ile Asp
1               5                   10                  15

Tyr Phe Asn Gly Ile Tyr Gly Phe Ala Thr Gly Ile Lys Asp Ile Met
            20                  25                  30

Asn Met Ile Phe Lys Thr Asp Thr Gly Gly Gly Asn Leu Thr Leu Asp
        35                  40                  45

Glu Ile Leu Lys Asn Gln Asp Leu Leu Asn Gln Ile Ser Asp Lys Leu
    50                  55                  60

Asp Gly Ile Asn Gly Asp Leu Gly Asp Leu Ile Ala Gln Gly Asn Leu
65                  70                  75                  80

Asn Ser Glu Leu Thr Lys Glu Leu Leu Lys Ile Ala Asn Glu Gln Asn
                85                  90                  95

Leu Met Leu Asn Asn Val Asn Ala Gln Leu Asn Ser Ile Asn Ser Thr
            100                 105                 110

Leu Asn Thr Tyr Leu Pro Lys Ile Thr Ser Met Leu Ser Glu Val Met
        115                 120                 125

Lys Gln Asn Tyr Val Leu Ser Leu Gln Ile Glu Phe Leu Ser Glu Gln
    130                 135                 140

Leu Gln Glu Ile Ser Asp Lys Leu Asp Val Ile Asn Leu Asn Val Leu
145                 150                 155                 160

Ile Asn Ser Thr Leu Thr Glu Ile Thr Pro Ala Tyr Gln Arg Ile Lys
                165                 170                 175
```

```
Tyr Val Asn Asp Lys Phe Asp Glu Leu Thr Ser Thr Val Glu Lys Asn
            180                 185                 190

Pro Lys Ile Asn Gln Asp Asn Phe Thr Glu Asp Val Ile Asp Asn Leu
        195                 200                 205

Thr Asp Leu Thr Glu Leu Ala Arg Ser Val Thr Arg Asn Asp Met Asp
    210                 215                 220

Ser Phe Glu Phe Tyr Ile Lys Thr Phe His Asp Val Met Ile Gly Asn
225                 230                 235                 240

Asn Leu Phe Ser Arg Ser Ala Leu Lys Thr Ala Ser Glu Leu Ile Ala
                245                 250                 255

Lys Glu Asn Ile His Thr Met Gly Ser Glu Ile Gly Asn Val Tyr Thr
            260                 265                 270

Phe Met Val Val Leu Thr Ser Leu Gln Ala Lys Ala Phe Leu Thr Leu
        275                 280                 285

Thr Ala Cys Arg Lys Leu Leu Gly Leu Thr Asp Ile Asp Tyr Thr Gln
    290                 295                 300

Ile Met Asn Glu Asn Leu Asn Arg Glu Lys Glu Glu Phe Arg Leu Asn
305                 310                 315                 320

Ile Leu Pro Thr Leu Ser Asn Asp Phe Ser Asn Pro Asn Tyr Thr Glu
                325                 330                 335

Thr Leu Gly Ser Asp Leu Val Asp Pro Ile Val Thr Leu Glu Ala Asp
            340                 345                 350

Pro Gly Tyr Ala Leu Ile Gly Phe Glu Ile Leu Asn Asp Pro Leu Pro
        355                 360                 365

Val Leu Lys Val Tyr Gln Ala Lys Leu Lys Pro Asn Tyr Gln Val Asp
    370                 375                 380

Lys Glu Ser Ile Met Glu Asn Ile Tyr Gly Asn Ile His Lys Leu Leu
385                 390                 395                 400

Cys Pro Lys Gln Arg His Gln Lys Tyr Tyr Ile Lys Asp Ile Thr Phe
                405                 410                 415

Pro Glu Gly Tyr Val Ile Thr Lys Ile Val Phe Glu Lys Lys Leu Asn
            420                 425                 430

Leu Leu Gly Tyr Glu Val Thr Ala Asn Leu Tyr Asp Pro Phe Thr Gly
        435                 440                 445

Ser Ile Asp Leu Asn Lys Thr Ile Leu Glu Ser Trp Lys Glu Glu Cys
    450                 455                 460

Cys Glu Glu Glu Cys Cys Glu Glu Glu Cys Cys Glu Glu Glu Cys Cys
465                 470                 475                 480

Glu Glu Leu Tyr Lys Ile Ile Glu Ala Asp Thr Asn Gly Val Tyr Met
                485                 490                 495

Pro Leu Gly Val Ile Ser Glu Thr Phe Leu Thr Pro Ile Tyr Ser Phe
            500                 505                 510

Lys Leu Ile Ile Asp Glu Arg Thr Lys Arg Ile Ser Leu Ala Gly Lys
        515                 520                 525

Ser Tyr Leu Arg Glu Ser Leu Leu Ala Thr Asp Leu Val Asn Lys Asp
    530                 535                 540

Thr Asn Leu Ile Pro Ser Pro Asn Gly Phe Ile Asn Ser Ile Val Glu
545                 550                 555                 560

Asn Trp Asn Ile Thr Ser Asp Asn Ile Glu Pro Trp Lys Ala Asn Asn
                565                 570                 575

Lys Asn Ala Tyr Val Asp Lys Thr Asp Asp Met Val Gly Phe Asn Ser
            580                 585                 590

Leu Tyr Thr His Lys Asp Gly Glu Phe Leu Gln Phe Ile Gly Ala Lys
```

```
        595                 600                 605

Leu Lys Ala Lys Thr Glu Tyr Ile Ile Gln Tyr Thr Val Lys Gly Ser
    610                 615                 620

Pro Glu Val Tyr Leu Lys Asn Asn Lys Gly Ile Phe Tyr Glu Asp Thr
625                 630                 635                 640

Thr Asn Lys Phe Asp Thr Phe Gln Thr Ile Thr Lys Lys Phe Asn Ser
                645                 650                 655

Gly Val Asp Pro Ser Glu Ile Tyr Leu Val Phe Lys Asn Gln Ile Gly
            660                 665                 670

Tyr Glu Ala Trp Gly Asn Lys Phe Ile Ile Leu Glu Ile Lys Ser Phe
        675                 680                 685

Glu Thr Leu Pro Gln Ile Leu Lys Pro Glu Asn Trp Met Pro Phe Gly
    690                 695                 700

Asn Ala Glu Ile Lys Glu Asp Gly Lys Ile Glu Ile Ser Gly Asn Gly
705                 710                 715                 720

Thr Met Thr Gln Asn Ile Gln Leu Glu Gln Asn Ser Lys Tyr His Leu
                725                 730                 735

Arg Phe Ser Val Lys Gly Lys Gly Arg Val Ala Ile Gln Thr Gln Ser
            740                 745                 750

Ser His Ile Asn Val Pro Ala Thr Asn Glu Glu Val Ser Thr Met Ile
        755                 760                 765

Thr Thr Arg Asn Leu Tyr Gly Glu Gly Met Ile Tyr Leu Phe Asn Asp
    770                 775                 780

Asp Val Glu Asn Ser Lys Val Ile Phe Ser Asp Val Ser Leu Val Lys
785                 790                 795                 800

Glu


<210> SEQ ID NO 10
<211> LENGTH: 2367
<212> TYPE: DNA
<213> ORGANISM: Artificial Sequence
<220> FEATURE:
<223> OTHER INFORMATION: vip3A-C Hybrid toxin coding sequence.

<400> SEQUENCE: 10

atgaacaaga ataatactaa attaagcaca agagccttac caagttttat tgattatttt      60

aatggcattt atggatttgc cactggtatc aaagacatta tgaacatgat ttttaaaacg     120

gatacaggtg gtgatctaac cctagacgaa attttaaaga atcagcagtt actaaatgat     180

atttctggta aattggatgg ggtgaatgga agcttaaatg atcttatcgc acagggaaac     240

ttaaatacag aattatctaa ggaaatatta aaaattgcaa atgaacaaaa tcaagtttta     300

aatgatgtta ataacaaact cgatgcgata aatacgatgc ttcgggtata tctacctaaa     360

attacctcta tgttgagtga tgtaatgaaa caaaattatg cgctaagtct gcaaatagaa     420

tacttaagta aacaattgca agagatttct gataagttgg atattattaa tgtaaatgta     480

cttattaact ctacacttac tgaaattaca cctgcgtatc aaaggattaa atatgtgaac     540

gaaaaatttg aggaattaac ttttgctaca gaaactagtt caaaagtaaa aaaggatggc     600

tctcctgcag atattcttga tgagttaact gagttaactg aactagcgaa aagtgtaaca     660

aaaaatgatg tggatggttt tgaattttac cttaatacat tccacgatgt aatggtagga     720

aataatttat tcgggcgttc agctttaaaa actgcatcgg aattaattac taaagaaaat     780

gtgaaaacaa gtggcagtga ggtcggaaat gtttataact tcttaattgt attaacagct     840

ctgcaagcaa aagcttttct tactttaaca acatgccgaa aattattagg cttagcagat     900
```

```
attgattata cttctattat gaatgaacat ttaaataagg aaaaagagga atttagagta    960
aacatcctcc ctacactttc taatactttt tctaatccta attatgcaaa agttaaagga   1020
agtgatgaag atgcaaagat gattgtggaa gctaaaccag gacatgcatt gattgggttt   1080
gaaattagta atgattcaat tacagtatta aaagtatatg aggctaagct aaaacaaaat   1140
tatcaagtcg ataaggattc cttatcggaa gttatttatg gtgatatgga taaattattg   1200
tgcccagatc aatctgaaca aatctattat acaaataaca tagtatttcc aaatgaatat   1260
gtaattacta aaattgattt cactaaaaaa atgaaaactt taagatatga ggtaacagcg   1320
aatttttatg attcttctac aggagaaatt gacttaaata agaaaaaagt agaatcaagt   1380
gaagcggagt atagaacgtt aagtgctaat gatgatgggg tgtatatgcc gttaggtgtc   1440
atcagtgaaa catttttgac tccgattaat gggtttggcc tccaagctga tgaaaattca   1500
agattaatta ctttaacatg taaatcatat ttaagagaac tactgctagc aacagactta   1560
agcaataaag aaactaaatt gatcgtcccg ccaagtggtt ttattagcaa tattgtagag   1620
aacgggtcca tagaagagga caatttagag ccgtggaaag caaataataa gaatgcgtat   1680
gtagatcata caggcggagt gaatggaact aaagctttat atgttcataa ggacggagga   1740
atttcacaat ttattggaga taagttaaaa ccgaaaactg agtatgtaat ccaatatact   1800
gttaaaggaa aaccttctat tcatttaaaa gatgaaaata ctggatatat tcattatgaa   1860
gatacaaata ataatttaga agattatcaa actattaata aacgttttac tacaggaact   1920
gatttaaagg gagtgtattt aattttaaaa agtcaaaatg gagatgaagc ttggggagat   1980
aaatttacaa ttttagaaat taagcctgcg gaggatttat taagcccaga attaattaat   2040
ccgaattctt ggattacgac tccaggggct agcatttcag gaaataaact tttcattaac   2100
ttggggacaa atgggacctt tagacaaagt ctttcattaa acagttattc aacttatagt   2160
ataagcttta ctgcatcagg accatttaat gtgacggtaa gaaattctag ggggagtatta  2220
tttgaacgaa gcaaccttat gtcttcaact agtcatattt ctgggacatt caaaactgaa   2280
tccaataata ccggattata tgtagaactt tcccgtcgct ctggtggtgg tggtcatata   2340
tcatttgaaa acgtttctat taaataa                                        2367
```

```
<210> SEQ ID NO 11
<211> LENGTH: 788
<212> TYPE: PRT
<213> ORGANISM: Artificial sequence
<220> FEATURE:
<223> OTHER INFORMATION: Hybrid Vip3A-C toxin

<400> SEQUENCE: 11

Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110
```

```
Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Ser Ile
```

```
    530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
    610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Lys Phe Thr Ile Leu Glu Ile Lys Pro Ala Glu Asp
            660                 665                 670

Leu Leu Ser Pro Glu Leu Ile Asn Pro Asn Ser Trp Ile Thr Thr Pro
        675                 680                 685

Gly Ala Ser Ile Ser Gly Asn Lys Leu Phe Ile Asn Leu Gly Thr Asn
    690                 695                 700

Gly Thr Phe Arg Gln Ser Leu Ser Leu Asn Ser Tyr Ser Thr Tyr Ser
705                 710                 715                 720

Ile Ser Phe Thr Ala Ser Gly Pro Phe Asn Val Thr Val Arg Asn Ser
                725                 730                 735

Arg Gly Val Leu Phe Glu Arg Ser Asn Leu Met Ser Ser Thr Ser His
            740                 745                 750

Ile Ser Gly Thr Phe Lys Thr Glu Ser Asn Asn Thr Gly Leu Tyr Val
        755                 760                 765

Glu Leu Ser Arg Arg Ser Gly Gly Gly Gly His Ile Ser Phe Glu Asn
    770                 775                 780

Val Ser Ile Lys
785
```

<210> SEQ ID NO 12
<211> LENGTH: 36
<212> TYPE: DNA
<213> ORGANISM: Artificial Sequence
<220> FEATURE:
<223> OTHER INFORMATION: 1F Forward primer

<400> SEQUENCE: 12
atgaacaaga ataatactaa attaagcaca agagcc 36

<210> SEQ ID NO 13
<211> LENGTH: 35
<212> TYPE: DNA
<213> ORGANISM: Artificial Sequence
<220> FEATURE:
<223> OTHER INFORMATION: 1R reverse primer

<400> SEQUENCE: 13
ctcaacatag aggtaatttt aggtagatat acccg 35

<210> SEQ ID NO 14
<211> LENGTH: 25
<212> TYPE: DNA
<213> ORGANISM: Artificial Sequence
<220> FEATURE:

<223> OTHER INFORMATION: Primer P3

<400> SEQUENCE: 14
gatgatgggg tgtatatgcc gttag 25

<210> SEQ ID NO 15
<211> LENGTH: 25
<212> TYPE: DNA
<213> ORGANISM: Artificial Sequence
<220> FEATURE:
<223> OTHER INFORMATION: Primer P4

<400> SEQUENCE: 15
aataaattgt gaaattcctc cgtcc 25

<210> SEQ ID NO 16
<211> LENGTH: 33
<212> TYPE: DNA
<213> ORGANISM: Artificial Sequence
<220> FEATURE:
<223> OTHER INFORMATION: Primer 4F

<400> SEQUENCE: 16
agtcaaaatg gagatcaagg ttggggagat aac 33

<210> SEQ ID NO 17
<211> LENGTH: 34
<212> TYPE: DNA
<213> ORGANISM: Artificial Sequence
<220> FEATURE:
<223> OTHER INFORMATION: Primer 4R

<400> SEQUENCE: 17
ttacttaata gagagatcgt ggaaatgtac aata 34

<210> SEQ ID NO 18
<211> LENGTH: 23
<212> TYPE: DNA
<213> ORGANISM: Artificial Sequence
<220> FEATURE:
<223> OTHER INFORMATION: Primer P5

<400> SEQUENCE: 18
aatggagatg aagcttgggg aga 23

<210> SEQ ID NO 19
<211> LENGTH: 25
<212> TYPE: DNA
<213> ORGANISM: Artificial Sequence
<220> FEATURE:
<223> OTHER INFORMATION: Primer P6

<400> SEQUENCE: 19
cgtggaaatg tacaatagga ccacc 25

<210> SEQ ID NO 20
<211> LENGTH: 25
<212> TYPE: DNA
<213> ORGANISM: Artificial Sequence
<220> FEATURE:
<223> OTHER INFORMATION: Primer Vip3CF4

<400> SEQUENCE: 20
gtttagaaga ttttcaaacc attac 25

<210> SEQ ID NO 21

<211> LENGTH: 21
<212> TYPE: DNA
<213> ORGANISM: Artificial Sequence
<220> FEATURE:
<223> OTHER INFORMATION: Primer T7

<400> SEQUENCE: 21
ttaatacgac tcactatagg g 21

<210> SEQ ID NO 22
<211> LENGTH: 34
<212> TYPE: DNA
<213> ORGANISM: Artificial Sequence
<220> FEATURE:
<223> OTHER INFORMATION: Primer Vip3Cc

<400> SEQUENCE: 22
tttatttaat agaaacgttt tcaaatgata tatg 34

<210> SEQ ID NO 23
<211> LENGTH: 38
<212> TYPE: DNA
<213> ORGANISM: Artificial Sequence
<220> FEATURE:
<223> OTHER INFORMATION: Primer Vip3Cn

<400> SEQUENCE: 23
caccatgaac aagaataata ctaaattaag cacaagag 38

<210> SEQ ID NO 24
<211> LENGTH: 38
<212> TYPE: DNA
<213> ORGANISM: Artificial Sequence
<220> FEATURE:
<223> OTHER INFORMATION: Primer Vip3A-N

<400> SEQUENCE: 24
caccatgaac aagaataata ctaaattaag cacaagag 38

<210> SEQ ID NO 25
<211> LENGTH: 29
<212> TYPE: DNA
<213> ORGANISM: Artificial Sequence
<220> FEATURE:
<223> OTHER INFORMATION: Primer Vip3A2050

<400> SEQUENCE: 25
taaagttatc tccccaagct tcatctcca 29

<210> SEQ ID NO 26
<211> LENGTH: 24
<212> TYPE: DNA
<213> ORGANISM: Artificial Sequence
<220> FEATURE:
<223> OTHER INFORMATION: Vip3C-C1

<400> SEQUENCE: 26
aatggagatg aagcttgggg agat 24

<210> SEQ ID NO 27
<211> LENGTH: 34
<212> TYPE: DNA
<213> ORGANISM: Artificial Sequence
<220> FEATURE:
<223> OTHER INFORMATION: Vip3C-C2

<400> SEQUENCE: 27
tttatttaat agaaacgttt tcaaatgata tatg 34

<210> SEQ ID NO 28
<211> LENGTH: 27
<212> TYPE: DNA
<213> ORGANISM: Artificial Sequence
<220> FEATURE:
<223> OTHER INFORMATION: Primer Vip3Za

<400> SEQUENCE: 28
ggcatttatg gatttgccac tggtatc 27

<210> SEQ ID NO 29
<211> LENGTH: 27
<212> TYPE: DNA
<213> ORGANISM: Artificial Sequence
<220> FEATURE:
<223> OTHER INFORMATION: Primer Vip3Zb

<400> SEQUENCE: 29
tcctttgata cgcaggtgta atttcag 27

<210> SEQ ID NO 30
<211> LENGTH: 13829
<212> TYPE: DNA
<213> ORGANISM: Artificial Sequence
<220> FEATURE:
<223> OTHER INFORMATION: pNOV2149

<400> SEQUENCE: 30
aagcttgcat gcctgcagtg cagcgtgacc cggtcgtgcc cctctctaga gataatgagc 60
attgcatgtc taagttataa aaaattacca catatttttt ttgtcacact tgtttgaagt 120
gcagtttatc tatctttata catatattta aactttactc tacgaataat ataatctata 180
gtactacaat aatatcagtg ttttagagaa tcatataaat gaacagttag acatggtcta 240
aaggacaatt gagtattttg acaacaggac tctacagttt tatcttttta gtgtgcatgt 300
gttctccttt ttttttgcaa atagcttcac ctatataata cttcatccat tttattagta 360
catccattta gggtttaggg ttaatggttt ttatagacta atttttttag tacatctatt 420
ttattctatt ttagcctcta aattaagaaa actaaaactc tattttagtt tttttattta 480
ataatttaga tataaaatag aataaaataa agtgactaaa aattaaacaa ataccctttta 540 agaaattaaa aaaactaagg aaacattttt cttgtttcga gtagataatg ccagcctgtt 600
aaacgccgtc gacgagtcta acggacacca accagcgaac cagcagcgtc gcgtcgggcc 660
aagcgaagca gacggcacgg catctctgtc gctgcctctg gacccctctc gagagttccg 720
ctccaccgtt ggacttgctc cgctgtcggc atccagaaat tgcgtggcgg agcggcagac 780
gtgagccggc acggcaggcg gcctcctcct cctctcacgg caccggcagc tacgggggat 840
tcctttccca ccgctccttc gctttccctt cctcgcccgc cgtaataaat agacaccccc 900
tccacaccct ctttccccaa cctcgtgttg ttcggagcgc acacacacac aaccagatct 960
cccccaaatc cacccgtcgg cacctccgct tcaaggtacg ccgctcgtcc tccccccccc 1020
cccctctcta ccttctctag atcggcgttc cggtccatgg ttagggcccg gtagttctac 1080
ttctgttcat gtttgtgtta gatccgtgtt tgtgttagat ccgtgctgct agcgttcgta 1140
cacggatgcg acctgtacgt cagacacgtt ctgattgcta acttgccagt gtttctcttt 1200
ggggaatcct gggatggctc tagccgttcc gcagacggga tcgatttcat gattttttttt 1260 gtttcgttgc atagggtttg gtttgccctt ttcctttatt tcaatatatg ccgtgcactt 1320

-continued

```
gtttgtcggg tcatcttttc atgctttttt ttgtcttggt tgtgatgatg tggtctggtt   1380

gggcggtcgt tctagatcgg agtagaattc tgtttcaaac tacctggtgg atttattaat   1440

tttggatctg tatgtgtgtg ccatacatat tcatagttac gaattgaaga tgatggatgg   1500

aaatatcgat ctaggatagg tatacatgtt gatgcgggtt ttactgatgc atatacagag   1560

atgctttttg ttcgcttggt tgtgatgatg tggtgtggtt gggcggtcgt tcattcgttc   1620

tagatcggag tagaatactg tttcaaacta cctggtgtat ttattaattt tggaactgta   1680

tgtgtgtgtc atacatcttc atagttacga gtttaagatg gatggaaata tcgatctagg   1740

ataggtatac atgttgatgt gggttttact gatgcatata catgatggca tatgcagcat   1800

ctattcatat gctctaacct tgagtaccta tctattataa taaacaagta tgttttataa   1860

ttattttgat cttgatatac ttggatgatg gcatatgcag cagctatatg tggatttttt   1920

tagccctgcc ttcatacgct atttatttgc ttggtactgt ttcttttgtc gatgctcacc   1980

ctgttgtttg gtgttacttc tgcagggatc caccatgaac aagaacaaca ccaagctctc   2040

cacccgcgcc ctcccgtcct tcatcgacta cttcaacggc atctacggct tcgccaccgg   2100

catcaaggac atcatgaaca tgatcttcaa gaccgacacc ggcggcaacc tcaccctcga   2160

cgagatcctc aagaaccagc agctcctcaa cgagatcagc ggcaagctcg acggcgtgaa   2220

cggctccctc aacgacctca tcgcccaggg caacctcaac accgagctgt ccaaggagat   2280

cctcaagatc gccaacgagc agaaccaggt gctcaacgac gtgaacaaca agctcgacgc   2340

catcaacacc atgctccaca tctacctccc gaagatcacc tccatgctct ccgacgtgat   2400

gaagcagaac tacgccctct ccctccagat cgagtacctc tccaagcagc tccaggagat   2460

cagcgacaag ctcgacatca tcaacgtgaa cgtgctcatc aactccaccc tcaccgagat   2520

caccccggcc taccagcgca tcaagtacgt gaacgagaag ttcgaggagc tgaccttcgc   2580

caccgagacc accctcaagg tgaagaagga ctcctccccg gccgacatcc tcgacgagct   2640

gaccgagctg accgagctgg ccaagtccgt gaccaagaac gacgtggacg gcttcgagtt   2700

ctacctcaac accttccacg acgtgatggt gggcaacaac ctcttcggcc gctccgccct   2760

caagaccgcc tccgagctga tcgccaagga gaacgtgaag acctccggct ccgaggtggg   2820

caacgtgtac aacttcctca tcgtgctcac cgccctgcag gccaaggcct tcctcaccct   2880

caccacctgc cgcaagctcc tcggcctcgc cggcatcgac tacacctcca tcatgaacga   2940

gcacctcaac aaggagaagg aggagttccg cgtgaacatc ctcccgaccc tctccaacac   3000

cttctccaac ccgaactacg ccaaggtgaa gggctccgac gaggacgcca agatgatcgt   3060

ggaggccaag ccgggccacg ccctcgtggg cttcgagatg tccaacgact ccatcaccgt   3120

gctcaaggtg tacgaggcca agctcaagca gaactaccag gtggacaagg actccctctc   3180

cgaggtgatc tacggcgaca ccgacaagct cttctgcccg gaccagtccg agcagatata   3240

ctacaccaac aacatcgtgt tcccgaacga gtacgtgatc accaagatcg acttcaccaa   3300

gaagatgaag accctccgct acgaggtgac cgccaacttc tacgactcct ccaccggcga   3360

gatcgacctc aacaagaaga aggtggagtc ctccgaggcc gagtaccgca ccctctccgc   3420

caacgacgac ggcgtgtaca tgccgctcgg cgtgatctcc gaaaccttcc tcaccccgat   3480

caacggcttc ggcctccagg ccgacgagaa ctcccgcctc atcaccctca cctgcaagtc   3540

ctacctccgc gagctgctcc tcgccaccga cctctccaac aaggagacca agctcatcgt   3600

gccgccgtcc ggcttcatct ccaacatcgt ggagaacggc tccatcgagg aggacaacct   3660

cgagccgtgg aaggccaaca acaagaacgc ctacgtggac cacaccggcg gcgtgaacgg   3720
```

```
caccaaggcc ctctacgtgc acaaggacgg cggcttctcc cagttcatcg gcgacaagct   3780
caagccgaag accgagtacg tgatccagta caccgtgaag ggcaagccgt ccatccacct   3840
caaggacgag aacaccggct acatccacta cgaggacacc aacaacaacc tcaaggacta   3900
ccagaccatc accaagcgct tcaccaccgg caccgacctc aagggcgtgt acctcatcct   3960
caagtcccag aacggcgacg aggcctgggg cgacaagttc accatccttg agatcaagcc   4020
ggccgaggac ctcctctccc cggagctgat caacccgaac tcctggatca ccaccccggg   4080
cgcctccatc tccggcaaca agctcttcat caacctcggc accaacggca ccttccgcca   4140
gtccctctcc ctcaactcct actccaccta ctccatctcc ttcaccgcct ccggcccgtt   4200
caacgtgacc gtgcgcaact cccgcagggt gctcttcgag cgctccaacc tcatgtcctc   4260
cacctcccac atctccggca ccttcaagac cgagtccaac aacaccggcc tctacgtgga   4320
gctgtcccgc cgctccggcg gcggcggcca catctccttc gagaacgtgt ccatcaagta   4380
gatctgagct ctagatcccc gaatttcccc gatcgttcaa acatttggca ataaagtttc   4440
ttaagattga atcctgttgc cggtcttgcg atgattatca tataatttct gttgaattac   4500
gttaagcatg taataattaa catgtaatgc atgacgttat ttatgagatg ggtttttatg   4560
attagagtcc cgcaattata catttaatac gcgatagaaa acaaaatata gcgcgcaaac   4620
taggataaat tatcgcgcgc ggtgtcatct atgttactag atcgggaatt gggtaccagc   4680
ttgcatgcct gcagtgcagc gtgacccggt cgtgcccctc tctagagata atgagcattg   4740
catgtctaag ttataaaaaa ttaccacata ttttttttgt cacacttgtt tgaagtgcag   4800
tttatctatc tttatacata tatttaaact ttactctacg aataatataa tctatagtac   4860
tacaataata tcagtgtttt agagaatcat ataaatgaac agttagacat ggtctaaagg   4920
acaattgagt attttgacaa caggactcta cagttttatc tttttagtgt gcatgtgttc   4980
tccttttttt ttgcaaatag cttcacctat ataatacttc atccatttta ttagtacatc   5040
catttagggt ttagggttaa tggtttttat agactaattt ttttagtaca tctattttat   5100
tctattttag cctctaaatt aagaaaacta aaactctatt ttagtttttt tatttaataa   5160
tttagatata aaatagaata aaataaagtg actaaaaatt aaacaaatac cctttaagaa   5220
attaaaaaaa ctaaggaaac atttttcttg tttcgagtag ataatgccag cctgttaaac   5280
gccgtcgacg agtctaacgg acaccaacca gcgaaccagc agcgtcgcgt cgggccaagc   5340
gaagcagacg gcacggcatc tctgtcgctg cctctggacc cctctcgaga gttccgctcc   5400
accgttggac ttgctccgct gtcggcatcc agaaattgcg tggcggagcg gcagacgtga   5460
gccggcacgg caggcggcct cctcctcctc tcacggcacc ggcagctacg gggggattcct   5520
ttcccaccgc tccttcgctt tcccttcctc gcccgcccgta ataaatagac acccccctcca   5580
caccctcttt ccccaacctc gtgttgttcg gagcgcacac acacacaacc agatctcccc   5640
caaatccacc cgtcggcacc tccgcttcaa ggtacgccgc tcgtcctccc cccccccccc   5700
tctctacctt ctctagatcg gcgttccggt ccatggttag ggcccggtag ttctacttct   5760
gttcatgttt gtgttagatc cgtgtttgtg ttagatccgt gctgctagcg ttcgtacacg   5820
gatgcgacct gtacgtcaga cacgttctga ttgctaactt gccagtgttt ctctttgggg   5880
aatcctggga tggctctagc cgttccgcag acgggatcga tttcatgatt ttttttgttt   5940
cgttgcatag ggtttggttt gcccttttcc tttatttcaa tatatgccgt gcacttgttt   6000
gtcgggtcat cttttcatgc ttttttttgt cttggttgtg atgatgtggt ctggttgggc   6060
ggtcgttcta gatcggagta gaattctgtt tcaaactacc tggtggattt attaattttg   6120
```

```
gatctgtatg tgtgtgccat acatattcat agttacgaat tgaagatgat ggatggaaat   6180
atcgatctag gataggtata catgttgatg cgggttttac tgatgcatat acagagatgc   6240
tttttgttcg cttggttgtg atgatgtggt gtggttgggc ggtcgttcat tcgttctaga   6300
tcggagtaga atactgtttc aaactacctg gtgtatttat taattttgga actgtatgtg   6360
tgtgtcatac atcttcatag ttacgagttt aagatggatg gaaatatcga tctaggatag   6420
gtatacatgt tgatgtgggt tttactgatg catatacatg atggcatatg cagcatctat   6480
tcatatgctc taaccttgag tacctatcta ttataataaa caagtatgtt ttataattat   6540
tttgatcttg atatacttgg atgatggcat atgcagcagc tatatgtgga tttttttagc   6600
cctgccttca tacgctattt atttgcttgg tactgtttct tttgtcgatg ctcaccctgt   6660
tgtttggtgt tacttctgca gggatccccg atcatgcaaa aactcattaa ctcagtgcaa   6720
aactatgcct ggggcagcaa aacggcgttg actgaacttt atggtatgga aaatccgtcc   6780
agccagccga tggccgagct gtggatgggc gcacatccga aaagcagttc acgagtgcag   6840
aatgccgccg gagatatcgt ttcactgcgt gatgtgattg agagtgataa atcgactctg   6900
ctcggagagg ccgttgccaa acgctttggc gaactgcctt tcctgttcaa agtattatgc   6960
gcagcacagc cactctccat tcaggttcat ccaaacaaac acaattctga aatcggtttt   7020
gccaaagaaa atgccgcagg tatcccgatg gatgccgccg agcgtaacta taaagatcct   7080
aaccacaagc cggagctggt ttttgcgctg acgcctttcc ttgcgatgaa cgcgtttcgt   7140
gaattttccg agattgtctc cctactccag ccggtcgcag gtgcacatcc ggcgattgct   7200
cactttttac aacagcctga tgccgaacgt ttaagcgaac tgttcgccag cctgttgaat   7260
atgcagggtg aagaaaaatc ccgcgcgctg gcgattttaa aatcggccct cgatagccag   7320
cagggtgaac cgtggcaaac gattcgttta atttctgaat tttacccgga agacagcggt   7380
ctgttctccc cgctattgct gaatgtggtg aaattgaacc ctggcgaagc gatgttcctg   7440
ttcgctgaaa caccgcacgc ttacctgcaa ggcgtggcgc tggaagtgat ggcaaactcc   7500
gataacgtgc tgcgtgcggg tctgacgcct aaatacattg atattccgga actggttgcc   7560
aatgtgaaat tcgaagccaa accggctaac cagttgttga cccagccggt gaaacaaggt   7620
gcagaactgg acttcccgat tccagtggat gattttgcct tctcgctgca tgaccttagt   7680
gataaagaaa ccaccattag ccagcagagt gccgccattt tgttctgcgt cgaaggcgat   7740
gcaacgttgt ggaaaggttc tcagcagtta cagcttaaac cgggtgaatc agcgtttatt   7800
gccgccaacg aatcaccggt gactgtcaaa ggccacggcc gtttagcgcg tgtttacaac   7860
aagctgtaag agcttactga aaaaattaac atctcttgct aagctgggag ctcgatccgt   7920
cgacctgcag atcgttcaaa catttggcaa taaagtttct taagattgaa tcctgttgcc   7980
ggtcttgcga tgattatcat ataatttctg ttgaattacg ttaagcatgt aataattaac   8040
atgtaatgca tgacgttatt tatgagatgg gtttttatga ttagagtccc gcaattatac   8100
atttaatacg cgatagaaaa caaaatatag cgcgcaaact aggataaatt atcgcgcgcg   8160
gtgtcatcta tgttactaga tctgctagcc ctgcaggaaa tttaccggtg cccgggcggc   8220
cagcatggcc gtatccgcaa tgtgttatta agttgtctaa gcgtcaattt gtttacacca   8280
caatatatcc tgccaccagc cagccaacag ctccccgacc ggcagctcgg cacaaaatca   8340
ccactcgata caggcagccc atcagaatta attctcatgt ttgacagctt atcatcgact   8400
gcacggtgca ccaatgcttc tggcgtcagg cagccatcgg aagctgtggt atggctgtgc   8460
aggtcgtaaa tcactgcata attcgtgtcg ctcaaggcgc actcccgttc tggataatgt   8520
```

-continued

```
tttttgcgcc gacatcataa cggttctggc aaatattctg aaatgagctg ttgacaatta   8580

atcatccggc tcgtataatg tgtggaattg tgagcggata acaatttcac acaggaaaca   8640

gaccatgagg gaagcgttga tcgccgaagt atcgactcaa ctatcagagg tagttggcgt   8700

catcgagcgc catctcgaac cgacgttgct ggccgtacat ttgtacggct ccgcagtgga   8760

tggcggcctg aagccacaca gtgatattga tttgctggtt acggtgaccg taaggcttga   8820

tgaaacaacg cggcgagctt tgatcaacga ccttttggaa acttcggctt cccctggaga   8880

gagcgagatt ctccgcgctg tagaagtcac cattgttgtg cacgacgaca tcattccgtg   8940

gcgttatcca gctaagcgcg aactgcaatt tggagaatgg cagcgcaatg acattcttgc   9000

aggtatcttc gagccagcca cgatcgacat tgatctggct atcttgctga caaaagcaag   9060

agaacatagc gttgccttgg taggtccagc ggcggaggaa ctctttgatc cggttcctga   9120

acaggatcta tttgaggcgc taaatgaaac cttaacgcta tggaactcgc cgcccgactg   9180

ggctggcgat gagcgaaatg tagtgcttac gttgtcccgc atttggtaca gcgcagtaac   9240

cggcaaaatc gcgccgaagg atgtcgctgc cgactgggca atggagcgcc tgccggccca   9300

gtatcagccc gtcatacttg aagctaggca ggcttatctt ggacaagaag atcgcttggc   9360

ctcgcgcgca gatcagttgg aagaatttgt tcactacgtg aaaggcgaga tcaccaaagt   9420

agtcggcaaa taaagctcta gtggatctcc gtacccccgg gggatctggc tcgcggcgga   9480

cgcacgacgc cggggcgaga ccataggcga tctcctaaat caatagtagc tgtaacctcg   9540

aagcgtttca cttgtaacaa cgattgagaa tttttgtcat aaaattgaaa tacttggttc   9600

gcatttttgt catccgcggt cagccgcaat tctgacgaac tgcccattta gctggagatg   9660

attgtacatc cttcacgtga aaatttctca agcgctgtga acaagggttc agattttaga   9720

ttgaaaggtg agccgttgaa acacgttctt cttgtcgatg acgacgtcgc tatgcggcat   9780

cttattattg aataccttac gatccacgcc ttcaaagtga ccgcggtagc cgacagcacc   9840

cagttcacaa gagtactctc ttccgcgacg gtcgatgtcg tggttgttga tctaaattta   9900

ggtcgtgaag atgggctcga gatcgttcgt aatctggcgg caaagtctga tattccaatc   9960

ataattatca gtggcgaccg ccttgaggag acggataaag ttgttgcact cgagctagga  10020

gcaagtgatt ttatcgctaa gccgttcagt atcagagagt ttctagcacg cattcgggtt  10080

gccttgcgcg tgcgccccaa cgttgtccgc tccaaagacc gacggtcttt ttgttttact  10140

gactggacac ttaatctcag gcaacgtcgc ttgatgtccg aagctggcgg tgaggtgaaa  10200

cttacggcag gtgagttcaa tcttctcctc gcgtttttag agaaaccccg cgacgttcta  10260

tcgcgcgagc aacttctcat tgccagtcga gtacgcgacg aggaggttta tgacaggagt  10320

atagatgttc tcattttgag gctgcgccgc aaacttgagg cagatccgtc aagccctcaa  10380

ctgataaaaa cagcaagagg tgccggttat ttctttgacg cggacgtgca ggtttcgcac  10440

ggggggacga tggcagcctg agccaattcc cagatccccg aggaatcggc gtgagcggtc  10500

gcaaaccatc cggcccggta caaatcggcg cggcgctggg tgatgacctg gtggagaagt  10560

tgaaggccgc gcaggccgcc cagcggcaac gcatcgaggc agaagcacgc cccggtgaat  10620

cgtggcaagc ggccgctgat cgaatccgca aagaatcccg gcaaccgccg gcagccggtg  10680

cgccgtcgat taggaagccg cccaagggcg acgagcaacc agattttttc gttccgatgc  10740

tctatgacgt gggcacccgc gatagtcgca gcatcatgga cgtggccgtt ttccgtctgt  10800

cgaagcgtga ccgacgagct ggcgaggtga tccgctacga gcttccagac gggcacgtag  10860

aggtttccgc agggccggcc ggcatggcca gtgtgtggga ttacgacctg gtactgatgg  10920
```

```
cggtttccca tctaaccgaa tccatgaacc gataccggga agggaaggga gacaagcccg  10980

gccgcgtgtt ccgtccacac gttgcggacg tactcaagtt ctgccggcga gccgatggcg  11040

gaaagcagaa agacgacctg gtagaaacct gcattcggtt aaacaccacg cacgttgcca  11100

tgcagcgtac gaagaaggcc aagaacggcc gcctggtgac ggtatccgag ggtgaagcct  11160

tgattagccg ctacaagatc gtaaagagcg aaaccgggcg gccggagtac atcgagatcg  11220

agctagctga ttggatgtac cgcgagatca cagaaggcaa gaacccggac gtgctgacgg  11280

ttcaccccga ttactttttg atcgatcccg gcatcggccg ttttctctac cgcctggcac  11340

gccgcgccgc aggcaaggca gaagccagat ggttgttcaa gacgatctac gaacgcagtg  11400

gcagcgccgg agagttcaag aagttctgtt tcaccgtgcg caagctgatc gggtcaaatg  11460

acctgccgga gtacgatttg aaggaggagg cggggcaggc tggcccgatc ctagtcatgc  11520

gctaccgcaa cctgatcgag ggcgaagcat ccgccggttc ctaatgtacg gagcagatgc  11580

tagggcaaat tgccctagca ggggaaaaag gtcgaaaagg tctctttcct gtggatagca  11640

cgtacattgg gaacccaaag ccgtacattg ggaaccggaa cccgtacatt gggaacccaa  11700

agccgtacat tgggaaccgg tcacacatgt aagtgactga tataaaagag aaaaaaggcg  11760

atttttccgc ctaaaactct ttaaaactta ttaaaactct taaaacccgc ctggcctgtg  11820

cataactgtc tggccagcgc acagccgaag agctgcaaaa agcgcctacc cttcggtcgc  11880

tgcgctccct acgccccgcc gcttcgcgtc ggcctatcgc ggccgctggc cgctcaaaaa  11940

tggctggcct acggccaggc aatctaccag ggcgcggaca agccgcgccg tcgccactcg  12000

accgccggcg ctgaggtctg cctcgtgaag aaggtgttgc tgactcatac caggcctgaa  12060

tcgccccatc atccagccag aaagtgaggg agccacggtt gatgagagct ttgttgtagg  12120

tggaccagtt ggtgattttg aacttttgct ttgccacgga acggtctgcg ttgtcgggaa  12180

gatgcgtgat ctgatccttc aactcagcaa aagttcgatt tattcaacaa agccgccgtc  12240

ccgtcaagtc agcgtaatgc tctgccagtg ttacaaccaa ttaaccaatt ctgattagaa  12300

aaactcatcg agcatcaaat gaaactgcaa tttattcata tcaggattat caataccata  12360

tttttgaaaa agccgtttct gtaatgaagg agaaaactca ccgaggcagt tccataggat  12420

ggcaagatcc tggtatcggt ctgcgattcc gactcgtcca acatcaatac aacctattaa  12480

tttcccctcg tcaaaaataa ggttatcaag tgagaaatca ccatgagtga cgactgaatc  12540

cggtgagaat ggcaaaagct ctgcattaat gaatcggcca acgcgcgggg agaggcggtt  12600

tgcgtattgg gcgctcttcc gcttcctcgc tcactgactc gctgcgctcg gtcgttcggc  12660

tgcggcgagc ggtatcagct cactcaaagg cggtaatacg gttatccaca gaatcagggg  12720

ataacgcagg aaagaacatg tgagcaaaag gccagcaaaa ggccaggaac cgtaaaaagg  12780

ccgcgttgct ggcgtttttc cataggctcc gcccccctga cgagcatcac aaaaatcgac  12840

gctcaagtca gaggtggcga aacccgacag gactataaag ataccaggcg tttccccctg  12900

gaagctccct cgtgcgctct cctgttccga ccctgccgct taccggatac ctgtccgcct  12960

ttctcccttc gggaagcgtg gcgctttctc atagctcacg ctgtaggtat ctcagttcgg  13020

tgtaggtcgt tcgctccaag ctgggctgtg tgcacgaacc ccccgttcag cccgaccgct  13080

gcgccttatc cggtaactat cgtcttgagt ccaacccggt aagacacgac ttatcgccac  13140

tggcagcagc cactggtaac aggattagca gagcgaggta tgtaggcggt gctacagagt  13200

tcttgaagtg gtggcctaac tacggctaca ctagaagaac agtatttggt atctgcgctc  13260

tgctgaagcc agttaccttc ggaaaaagag ttggtagctc ttgatccggc aaacaaacca  13320
```

ccgctggtag cggtggtttt tttgtttgca agcagcagat tacgcgcaga aaaaaaggat 13380
ctcaagaaga tcctttgatc ttttctacgg ggtctgacgc tcagtggaac gaaaactcac 13440
gttaagggat tttggtcatg agattatcaa aaaggatctt cacctagatc cttttgatcc 13500
ggaattaatt cctgtggttg gcatgcacat acaaatggac gaacggataa accttttcac 13560
gcccttttaa atatccgatt attctaataa acgctctttt ctcttaggtt tacccgccaa 13620
tatatcctgt caaacactga tagtttaaac tgaaggcggg aaacgacaat ctgatcatga 13680
gcggagaatt aagggagtca cgttatgacc cccgccgatg acgcgggaca agccgtttta 13740
cgtttggaac tgacagaacc gcaacgctgc aggaattggc cgcagcggcc atttaaatca 13800
attgggcgcg ccgaattcga gctcggtac 13829

<210> SEQ ID NO 31
<211> LENGTH: 2367
<212> TYPE: DNA
<213> ORGANISM: Bacillus thuringiensis
<220> FEATURE:
<221> NAME/KEY: misc_feature
<222> LOCATION: (1)..(2367)
<223> OTHER INFORMATION: Variant Vip3C coding sequence

<400> SEQUENCE: 31
atgaatatga ataatactaa attaaacgca agggccctac cgagttttat tgattatttt 60
aatggcattt atggatttgc cactggtatc aaagacatta tgaatatgat ttttaaaacg 120
gatacaggtg gtaatctaac cttagacgaa atcctaaaga atcagcagtt actaaatgag 180
atttctggta aattggatgg ggtaaatggg agcttaaatg atcttatcgc acagggaaac 240
ttaaatacag aattatctaa ggaaatctta aaaattgcaa atgaacagaa tcaagtctta 300
aatgatgtta ataacaaact cgatgcgata aatacgatgc ttcatatata tctacctaaa 360
attacatcta tgttaagtga tgtaatgaag caaaattatg cgctaagtct gcaaatagaa 420
tacttaagta agcaattgca agaaatttct gataaattag atattattaa cgtaaatgtt 480
cttattaact ctacacttac tgaaattaca cctgcatatc aacggattaa atatgtgaat 540
gaaaaatttg aagaattaac ttttgctaca gaaaccactt taaaagtaaa aaaggatagc 600
tcgcctgctg atattcttga tgagttaact gaattaactg aactagcgaa aagtgttaca 660
aaaaatgacg ttgatggttt tgaattttac cttaatacat tccacgatgt aatggtagga 720
aataatttat tcgggcgttc agctttaaaa actgcttcag aattaattgc taaagaaaat 780
gtgaaaacaa gtggcagtga agtaggaaat gtttataatt tcttaattgt attaacagct 840
ctacaagcaa aagcttttct tactttaaca acatgccgaa aattattagg cttagcagat 900
attgattata cttctattat gaatgaacat ttaaataagg aaaaagagga atttagagta 960
aacatccttc ctacactttc taatactttt tctaatccta attatgcaaa agttaaagga 1020
agtgatgaag atgcaaagat gattgtggaa gctaaaccag gacatgcatt ggttgggttt 1080
gaaatgagca atgattcaat cacagtatta aaagtatatg aggctaagct aaaacaaaat 1140
tatcaagttg ataaggattc cttatcggag gttatttatg gtgatacgga taaattattt 1200
tgtccagatc aatctgaaca aatatattat acaaataaca tagtattccc aaatgaatat 1260
gtaattacta aaattgattt cactaaaaaa atgaaaactt taagatatga ggtaacagcg 1320
aatttttatg attcttctac aggagaaatt gacttaaata agaaaaaagt agaatcaagt 1380
gaagcggagt atagaacgtt aagtgctaat gatgatggag tgtatatgcc attaggtgtc 1440
atcagtgaaa catttttgac tccgataaat gggtttggcc tccaagctga tgaaaattca 1500

```
agattaatta ctttaacatg taaatcatat ttaagagaac tactgctagc aacagactta   1560

agcaataaag aaactaaatt gatcgtccca ccaagtggtt ttattagcaa tattgtagag   1620

aacgggtcca tagaagagga caatttagag ccgtggaaag caaataataa gaatgcgtat   1680

gtagatcata caggcggagt gaatggaact aaagctttat atgttcataa ggacggagga   1740

ttttcacaat ttattggaga taagttaaaa ccgaaaactg agtatgtaat ccaatatact   1800

gttaaaggaa aaccttctat tcatttaaaa gatgaaaata ctggatatat tcattatgaa   1860

gatacaaata ataatttaaa agattatcaa actattacta aacgttttac tacaggaact   1920

gatttaaagg gagtgtattt aattttaaaa agtcaaaatg gagatgaagc ttggggagat   1980

aaatttacaa ttttagaaat taagcctgcg gaggatttat taagcccaga attaattaat   2040

ccgaattctt ggattacgac tccaggggct agcatttcag gaaataaact tttcattaac   2100

ttggggacaa atgggacctt tagacaaagt ctttcattaa acagttattc aacttatagt   2160

ataagcttta ctgcatcagg accatttaat gtgacggtaa gaaattctag ggaagtatta   2220

tttgaacgaa gcaaccttat gtcttcaact agtcatattt ctgggacatt caaaactgaa   2280

tccaataata ccggattata tgtagaactt tcccgtcgct ctggtggtgg tggtcatata   2340

tcatttgaaa acgtttctat taaataa                                       2367
```

```
<210> SEQ ID NO 32
<211> LENGTH: 788
<212> TYPE: PRT
<213> ORGANISM: Bacillus thuringiensis
<220> FEATURE:
<221> NAME/KEY: MISC_FEATURE
<222> LOCATION: (1)..(788)
<223> OTHER INFORMATION: Vip3C-11230 toxin

<400> SEQUENCE: 32

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
        195                 200                 205
```

```
Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Val Gly Phe Glu Met Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Thr Asp Lys Leu Phe
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Ser Ile
    530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Phe Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
    610                 615                 620

Asn Leu Lys Asp Tyr Gln Thr Ile Thr Lys Arg Phe Thr Thr Gly Thr
```

```
625                 630                 635                 640

Asp Leu Lys Gly Val Tyr Leu Ile Leu Lys Ser Gln Asn Gly Asp Glu
                645                 650                 655

Ala Trp Gly Asp Lys Phe Thr Ile Leu Glu Ile Lys Pro Ala Glu Asp
            660                 665                 670

Leu Leu Ser Pro Glu Leu Ile Asn Pro Asn Ser Trp Ile Thr Thr Pro
        675                 680                 685

Gly Ala Ser Ile Ser Gly Asn Lys Leu Phe Ile Asn Leu Gly Thr Asn
    690                 695                 700

Gly Thr Phe Arg Gln Ser Leu Ser Leu Asn Ser Tyr Ser Thr Tyr Ser
705                 710                 715                 720

Ile Ser Phe Thr Ala Ser Gly Pro Phe Asn Val Thr Val Arg Asn Ser
                725                 730                 735

Arg Glu Val Leu Phe Glu Arg Ser Asn Leu Met Ser Ser Thr Ser His
            740                 745                 750

Ile Ser Gly Thr Phe Lys Thr Glu Ser Asn Asn Thr Gly Leu Tyr Val
        755                 760                 765

Glu Leu Ser Arg Arg Ser Gly Gly Gly Gly His Ile Ser Phe Glu Asn
    770                 775                 780

Val Ser Ile Lys
785


<210> SEQ ID NO 33
<211> LENGTH: 2367
<212> TYPE: DNA
<213> ORGANISM: Artificial Sequence
<220> FEATURE:
<223> OTHER INFORMATION: Maize optimized Vip3C-11230

<400> SEQUENCE: 33

atgaacaaga acaacaccaa gctcaacgcc cgcgccctcc cgtccttcat cgactacttc      60

aacggcatct acggcttcgc caccggcatc aaggacatca tgaacatgat cttcaagacc     120

gacaccggcg gcaacctcac cctcgacgag atcctcaaga accagcagct cctcaacgag     180

atcagcggca agctcgacgg cgtgaacggc tccctcaacg acctcatcgc ccagggcaac     240

ctcaacaccg agctgtccaa ggagatcctc aagatcgcca acgagcagaa ccaggtgctc     300

aacgacgtga acaacaagct cgacgccatc aacaccatgc tccacatcta cctcccgaag     360

atcacctcca tgctctccga cgtgatgaag cagaactacg ccctctccct ccagatcgag     420

tacctctcca agcagctcca ggagatcagc gacaagctcg acatcatcaa cgtgaacgtg     480

ctcatcaact ccaccctcac cgagatcacc ccggcctacc agcgcatcaa gtacgtgaac     540

gagaagttcg aggagctgac cttcgccacc gagaccaccc tcaaggtgaa gaaggactcc     600

tccccggccg acatcctcga cgagctgacc gagctgaccg agctggccaa gtccgtgacc     660

aagaacgacg tggacggctt cgagttctac ctcaacacct tccacgacgt gatggtgggc     720

aacaacctct tcggccgctc cgccctcaag accgcctccg agctgatcgc caaggagaac     780

gtgaagacct ccggctccga ggtgggcaac gtgtacaact tcctcatcgt gctcaccgcc     840

ctgcaggcca aggccttcct caccctcacc acctgccgca agctcctcgg cctcgccgac     900

atcgactaca cctccatcat gaacgagcac ctcaacaagg agaaggagga gttccgcgtg     960

aacatcctcc cgaccctctc caacaccttc tccaacccga actacgccaa ggtgaagggc    1020

tccgacgagg acgccaagat gatcgtggag gccaagccgg gccacgccct cgtgggcttc    1080

gagatgtcca acgactccat caccgtgctc aaggtgtacg aggccaagct caagcagaac    1140
```

-continued

```
taccaggtgg acaaggactc cctctccgag gtgatctacg gcgacaccga caagctcttc   1200

tgcccggacc agtccgagca gatatactac accaacaaca tcgtgttccc gaacgagtac   1260

gtgatcacca agatcgactt caccaagaag atgaagaccc tccgctacga ggtgaccgcc   1320

aacttctacg actcctccac cggcgagatc gacctcaaca agaagaaggt ggagtcctcc   1380

gaggccgagt accgcaccct ctccgccaac gacgacggcg tgtacatgcc gctcggcgtg   1440

atctccgaaa ccttcctcac cccgatcaac ggcttcggcc tccaggccga cgagaactcc   1500

cgcctcatca ccctcacctg caagtcctac ctccgcgagc tgctcctcgc caccgacctc   1560

tccaacaagg agaccaagct catcgtgccg ccgtccggct tcatctccaa catcgtggag   1620

aacggctcca tcgaggagga caacctcgag ccgtggaagg ccaacaacaa gaacgcctac   1680

gtggaccaca ccggcggcgt gaacggcacc aaggccctct acgtgcacaa ggacggcggc   1740

ttctcccagt tcatcggcga caagctcaag ccgaagaccg agtacgtgat ccagtacacc   1800

gtgaagggca agccgtccat ccacctcaag gacgagaaca ccggctacat ccactacgag   1860

gacaccaaca acaacctcaa ggactaccag accatcacca agcgcttcac caccggcacc   1920

gacctcaagg gcgtgtacct catcctcaag tcccagaacg gcgacgaggc ctggggcgac   1980

aagttcacca tccttgagat caagccggcc gaggacctcc tctccccgga gctgatcaac   2040

ccgaactcct ggatcaccac cccgggcgcc tccatctccg gcaacaagct cttcatcaac   2100

ctcggcacca acggcacctt ccgccagtcc ctctccctca actcctactc cacctactcc   2160

atctccttca ccgcctccgg cccgttcaac gtgaccgtgc gcaactcccg cgaggtgctc   2220

ttcgagcgct ccaacctcat gtcctccacc tcccacatct ccggcacctt caagaccgag   2280

tccaacaaca ccggcctcta cgtggagctg tcccgccgct ccggcggcgg cggccacatc   2340

tccttcgaga acgtgtccat caagtag                                     2367
```

VIP3 TOXINS AND METHODS OF USE

FIELD OF THE INVENTION

The present invention relates to novel Vip3 toxins from *Bacillus thuringiensis*, nucleic acid sequences whose expression results in said toxins, and methods of making and methods of using the toxins and corresponding nucleic acid sequences to control insects.

BACKGROUND OF THE INVENTION

Plant pests are a major factor in the loss of the world's important agricultural crops. About $8 billion are lost every year in the U.S. alone due to infestations of non-mammalian pests including insects. In addition to losses in field crops, insect pests are also a burden to vegetable and fruit growers, to producers of ornamental flowers, and to home gardeners.

Insect pests are mainly controlled by intensive applications of chemical pesticides, which are active through inhibition of insect growth, prevention of insect feeding or reproduction, or cause death. Good insect control can thus be reached, but these chemicals can sometimes also affect other, beneficial insects. Another problem resulting from the wide use of chemical pesticides is the appearance of resistant insect varieties. This has been partially alleviated by various resistance management practices, but there is an increasing need for alternative pest control agents. Biological pest control agents, such as *Bacillus thuringiensis* strains expressing pesticidal toxins like δ-endotoxins, have also been applied to crop plants with satisfactory results, offering an alternative or compliment to chemical pesticides. The genes coding for some of these δ-endotoxins have been isolated and their expression in heterologous hosts have been shown to provide another tool for the control of economically important insect pests. In particular, the expression of insecticidal toxins in transgenic plants, such as *Bacillus thuringiensis* δ-endotoxins, has provided efficient protection against selected insect pests, and transgenic plants expressing such toxins have been commercialized, allowing farmers to reduce applications of chemical insect control agents.

Other, non-endotoxin genes and the proteins they encode have now been identified. U.S. Pat. Nos. 5,877,012, 6,107,279, 6,137,033, and 6,291,156, as well as Estruch et al. (1996, Proc. Natl. Acad. Sci. 93:5389-5394) and Yu et al. (1997, Appl. Environ. Microbiol. 63:532-536), herein incorporated by reference, describe a new class of insecticidal proteins called Vip3. Vip3 genes encode approximately 88 kDa proteins that are produced and secreted by *Bacillus* during its vegetative stages of growth (vegetative insecticidal proteins, VIP). The Vip3A protein possesses insecticidal activity against a wide spectrum of lepidopteran pests, including, but not limited to, black cutworm (BCW, *Agrotis epsilon*), fall armyworm (FAW, *Spodoptera frugiperda*), tobacco budworm (TBW, *Heliothis virescens*), and corn earworm (CEW, *Helicoverpa zea*). More recently, plants expressing the Vip3A protein have been found to be resistant to feeding damage caused by hemipteran insect pests. Thus, the Vip3A protein displays a unique spectrum of insecticidal activities. Other disclosures, WO 98/18932, WO 98/33991, WO 98/00546, and WO 99/57282, have also now identified homologues of the Vip3 class of proteins.

The continued use of chemical and biological agents to control insect pests heightens the chance for insects to develop resistance to such control measures. Also, only a few specific insect pests are controllable with each control agent.

Therefore, there remains a need to discover new and effective pest control agents that provide an economic benefit to farmers and that are environmentally acceptable. Particularly needed are control agents that are targeted to a wide spectrum of economically important insect pests, to control agents that efficiently control insect strains that are or could become resistant to existing insect control agents, and those with increased potency compared to current control agents. Furthermore, agents whose application minimizes the burden on the environment are desirable.

SUMMARY

The present invention addresses the need for novel pest control agents by providing new genes and toxins that are distinct from those disclosed in U.S. Pat. Nos. 5,877,012, 6,107,279, and 6,137,033, and Estruch et al. (1996), and Yu et al. (1997), as well as WO 98/18932, WO 99/33991, WO 99/5782, and WO 98/00546.

Within the present invention, compositions and methods for controlling plant pests are provided. In particular, novel vip3 nucleic acid sequences isolated from *Bacillus thuringiensis*, and sequences substantially identical thereto, whose expression results in pesticidal toxins with toxicity to economically important insect pests, particularly insect pests that infest plants, are provided. The invention is further drawn to the novel pesticidal toxins resulting from the expression of the nucleic acid sequences, and to compositions and formulations containing the pesticidal toxins, which are capable of inhibiting the ability of insect pests to survive, grow and reproduce, or of limiting insect-related damage or loss to crop plants. The invention is also drawn to methods of using the nucleic acid sequences, for example in making hybrid toxins with enhanced pesticidal activity or in a recombinogenic procedure such as DNA shuffling. The invention is further drawn to a method of making the toxins and to methods of using the nucleic acid sequences, for example in microorganisms to control insects or in transgenic plants to confer protection from insect damage, and to a method of using the pesticidal toxins, and compositions and formulations comprising the pesticidal toxins, for example applying the pesticidal toxins or compositions or formulations to insect-infested areas, or to prophylactically treat insect-susceptible areas or plants to confer protection against the insect pests.

The nucleotide sequences of the present invention can be engineered using methods generally known in the art in order to alter the nucleotide sequences for a variety of purposes including, but not limited to, broadening the spectrum of pesticidal activity, or increasing the specific activity against a specific pest. DNA shuffling by random fragmentation and PCR reassembly of gene fragments and synthetic oligonucleotides may be used to engineer the nucleotide sequences.

The novel pesticidal toxins described herein are highly active against insects. For example, a number of economically important insect pests, such as the lepidopterans *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Diatraea grandiosella* (southwestern corn borer), *Diatraea saccharalis* (sugarcane borer), *Helicoverpa punctigera* (native budworm) and *Helicoverpa armigera* (cotton bollworm) can be controlled by the pesticidal toxins. The pesticidal toxins can be used singly or in combination with other insect control strategies to confer maximal pest control efficiency with minimal environmental impact.

According to one aspect, the present invention provides an isolated nucleic acid molecule comprising a nucleotide sequence that encodes a toxin that is active against insects, wherein the nucleotide sequence: (a) has a compliment that hybridizes to nucleotides 1981-2367 of SEQ ID NO: 1 in 7% sodium dodecyl sulfate (SDS), 0.5 M $NaPO_4$, 1 mM EDTA at 50° C. with washing in 0.1× SSC, 0.1% SDS at 65° C.; or (b) is isocoding with the nucleotide sequence of (a); or (c) comprises a consecutive 20 base pair nucleotide portion identical in sequence to a consecutive 20 base pair nucleotide portion of a nucleotide sequence of (a) or (b); or (d) has at least 93% sequence identity with SEQ ID NO: 1; or (e) encodes an amino acid sequence having at least 91% sequence identity with SEQ ID NO: 2.

In one embodiment of this aspect, the isolated nucleic acid molecule comprises a nucleotide sequence that has a compliment that hybridizes to nucleotides 1981-2367 of SEQ ID NO: 1 in 7% sodium dodecyl sulfate (SDS), 0.5 M $NaPO_4$, 1 mM EDTA at 50° C. with washing in 0.1× SSC, 0.1% SDS at 65° C.

In another embodiment of this aspect, the isolated nucleic acid molecule comprises a nucleotide sequence that is isocoding with a nucleotide sequence having a compliment that hybridizes to nucleotides 1981-2367 of SEQ ID NO: 1 in 7% sodium dodecyl sulfate (SDS), 0.5 M $NaPO_4$, 1 mM EDTA at 50° C. with washing in 0.1× SSC, 0.1% SDS at 65° C.

In yet another embodiment, the isolated nucleic acid molecule comprises a consecutive 20 base pair nucleotide portion identical in sequence to a consecutive 20 base pair nucleotide portion of nucleotides 1981-2367 of the nucleotide sequences set forth in SEQ ID NO: 1 or SEQ ID NO: 3.

In another embodiment, the isolated nucleic acid molecule comprises a nucleotide sequence that has at least 75% sequence identity with nucleotides 1981-2367 of SEQ ID NO: 1. Preferably, the isolated nucleic acid molecule comprises a nucleotide sequence that has at least 85% sequence identity with nucleotides 1981-2367 of SEQ ID NO: 1. More preferably, the isolated nucleic acid molecule comprises a nucleotide sequence that has at least 95% sequence identity with nucleotides 1981-2367 of SEQ ID NO: 1. Even more preferably, the isolated nucleic acid molecule comprises a nucleotide sequence that has at least 99% sequence identity with nucleotides 1981-2367 of SEQ ID NO: 1. Most preferably, the isolated nucleic acid molecule comprises nucleotides 1981-2367 of SEQ ID NO: 1 or SEQ ID NO: 3.

In another embodiment, the isolated nucleic acid molecule comprises a nucleotide sequence that has at least 93% sequence identity with SEQ ID NO: 1. Preferably, the isolated nucleic acid molecule comprises a nucleotide sequence that has at least 95% sequence identity with SEQ ID NO: 1. More preferably, the isolated nucleic acid molecule comprises a nucleotide sequence that has at least 99% sequence identity with SEQ ID NO: 1. Most preferably, the isolated nucleic acid molecule comprises nucleotides 1-2367 of a nucleotide sequence selected from the group consisting of SEQ ID NO: 1, SEQ ID NO: 3, SEQ ID NO: 10, SEQ ID NO: 31, and SEQ ID NO: 33.

In one embodiment of the present invention, the isolated nucleic acid molecule encodes a toxin comprising an amino acid sequence with at least 75% identity with amino acids 661-788 of the amino acid sequence of SEQ ID NO: 2. Preferably, the isolated nucleic acid molecule encodes a toxin comprising an amino acid sequence which has at least 85% identity with amino acids 661-788 of the amino acid sequence of SEQ ID NO: 2. More preferably, the isolated nucleic acid molecule encodes a toxin comprising an amino acid sequence which has at least 95% identity with amino acids 661-788 of the amino acid sequence of SEQ ID NO: 2. Even more preferably, the isolated nucleic acid molecule encodes a toxin comprising an amino acid sequence which has at least 99% identity with amino acids 661-788 of the amino acid sequence of SEQ ID NO: 2. Most preferably, the isolated nucleic acid molecule encodes a toxin comprising amino acids 661-788 of SEQ ID NO: 2.

In another embodiment, the isolated nucleic acid molecule encodes a toxin comprising an amino acid sequence which has at least 91% identity to the amino acid sequence set forth in SEQ ID NO: 2. Preferably, the isolated nucleic acid molecule encodes a toxin comprising an amino acid sequence which has at least 95% identity to the amino acid sequence set forth in SEQ ID NO: 2. More preferably, the isolated nucleic acid molecule encodes a toxin comprising an amino acid sequence which has at least 99% identity to the amino acid sequence set forth in SEQ ID NO: 2. Most preferably, the isolated nucleic acid molecule encodes a toxin comprising the amino acid sequence set forth in SEQ ID NO: 2 or SEQ ID NO: 12.

In one embodiment, the isolated nucleic acid molecule is comprised in a *Bacillus thuringiensis* isolate selected from the group consisting of C1674, designated NRRL accession B-30556; and C536, designated NRRL accession B-30557.

In another embodiment, the isolated nucleic acid molecule comprises the approximately 2.4 kb DNA fragment comprised in an *E. coli* clone selected from the group consisting of pNOV3910, designated NRRL accession B-30553; pNOV3911, designated NRRL accession B-30552; pNOV3906, designated NRRL accession B-30555; pNOV3905, designated NRRL accession B-30554; and pNOV3912, designated NRRL accession B-30551.

According to one embodiment of the invention, the isolated nucleic acid molecule encodes a toxin that is active against a lepidopteran insect. Preferably, according to this embodiment, the toxin has activity against *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth).

The present invention also provides a chimeric gene comprising a heterologous promoter sequence operatively linked to the nucleic acid molecule of the invention. Further, the present invention provides a recombinant vector comprising such a chimeric gene. Still further, the present invention provides a transgenic host cell comprising such a chimeric gene. A transgenic host cell according to this aspect of the invention may be an animal cell, an animal virus, a plant virus, a bacterial cell, a yeast cell or a plant cell, preferably, a plant cell. Even further, the present invention provides a transgenic plant comprising such a plant cell. A transgenic plant according to this aspect of the invention may be sorghum, wheat, sunflower, tomato, cole crops, cotton, rice, soybean, sugar beet, sugarcane, tobacco, barley, oilseed rape or maize, preferably maize and cotton. Still further, the present invention provides seed from the group of transgenic plants consisting of sorghum, wheat, sunflower, tomato, cole crops, cotton, rice, soybean, sugar beet, sugarcane, tobacco, barley, oilseed rape and maize. In a particularly preferred embodiment, the seed is from a transgenic maize plant or transgenic cotton plant.

Also provided by the invention are transgenic plants of the invention further comprising a second nucleic acid sequence or groups of nucleic acid sequences that encode a second pesticidal principle. Particularly preferred second nucleic acid sequences are those that encode a δ-endotoxin, those that encode another Vegetative Insecticidal Protein toxin or those that encode a pathway for the production of a non-proteinaceous pesticidal principle.

In yet another aspect, the present invention provides toxins produced by the expression of the nucleic acid molecules of the present invention.

In a preferred embodiment, the toxin is produced by the expression of the nucleic acid molecule comprising nucleotides 1-2367 of a nucleotide sequence selected from the group consisting of SEQ ID NO: 1, SEQ ID NO: 3, and SEQ ID NO: 10.

In another embodiment, the toxins of the invention are active against lepidopteran insects, preferably against *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth).

In one embodiment, the toxins of the present invention are produced by a *Bacillus thuringiensis* isolate selected from the group consisting of C1674, designated NRRL accession B-30556; and C536, designated NRRL accession B-30557.

In another embodiment, the toxins are produced by an *E. coli* clone selected from the group consisting of pNOV3910, designated NRRL accession B-30553; pNOV3911, designated NRRL accession B-30552; pNOV3906, designated NRRL accession B-30555; pNOV3905, designated NRRL accession B-30554; and pNOV3912, designated NRRL accession B-30551.

In one embodiment, a toxin of the present invention comprises an amino acid sequence which has at least 75% identity with amino acids 661-788 of the amino acid sequence of SEQ ID NO: 2. Preferably, the toxin comprises an amino acid sequence which has at least 85% identity with amino acids 661-788 of the amino acid sequence of SEQ ID NO: 2. More preferably, the toxin comprises an amino acid sequence which has at least 95% identity with amino acids 661-788 of the amino acid sequence of SEQ ID NO: 2. Even more preferably, the toxin comprises an amino acid sequence that has at least 99% identity with amino acids 661-788 of the amino acid sequence of SEQ ID NO: 2. Most preferably, the toxin comprises amino acids 661-788 of SEQ ID NO: 2.

In another embodiment, a toxin of the present invention comprises an amino acid sequence which has at least 91% identity with the amino acid sequence set forth in SEQ ID NO: 2. Preferably, the toxin comprises an amino acid sequence which has at least 95% identity with the amino acid sequence set forth in SEQ ID NO: 2. More preferably, the toxin comprises an amino acid sequence which has at least 99% identity with the amino acid sequence set forth in SEQ ID NO: 2. Most preferably, the toxin comprises the amino acid sequence set forth in SEQ ID NO: 2, SEQ ID NO: 11, or SEQ ID NO: 32.

The present invention also provides a composition comprising an effective insect-controlling amount of a toxin according to the invention.

In another aspect, the present invention provides a method of producing a toxin that is active against insects, comprising: (a) obtaining a transgenic host cell comprising a chimeric gene, which itself comprises a heterologous promoter sequence operatively linked to the nucleic acid molecule of the invention; and (b) expressing the nucleic acid molecule in the transgenic cell, which results in at least one toxin that is active against insects.

In a further aspect, the present invention provides a method of producing an insect-resistant transgenic plant, comprising introducing a nucleic acid molecule of the invention into the transgenic plant, wherein the nucleic acid molecule is expressible in the transgenic plant in an effective amount to control insects. According to one embodiment, the insects are lepidopteran insects, preferably selected from the group consisting of: *Ostrinia nubilalis* (European corn borer), *Plutella xylostella* (diamondback moth), *Spodoptera frugiperda* (fall armyworm), *Agrotis epsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth).

In still a further aspect, the present invention provides a method of controlling insects comprising delivering to the insects an effective amount of a toxin of the present invention. According to one embodiment, the insects are lepidopteran insects, preferably selected from the group consisting of: *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth). Preferably, the toxin is delivered to the insects orally. In one preferred embodiment, the toxin is delivered orally through a transgenic plant comprising a nucleic acid sequence that expresses a toxin of the present invention.

The present invention also provides hybrid toxins active against insects, wherein the hybrid toxins are encoded by a nucleic acid molecule comprising a nucleotide sequence according to the invention.

In one embodiment, the hybrid toxins of the invention are active against lepidopteran insects, preferably against *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth).

In another embodiment, the hybrid toxin is encoded by the approximately 2.4 kb DNA fragment comprised in the *E. coli* clone pNOV3912, designated NRRL accession B-30551. In a preferred embodiment, the hybrid toxin is encoded by the nucleotide sequence set forth in SEQ ID NO: 10.

The present invention also provides a composition comprising an insecticidally effective amount of a hybrid toxin according to the invention.

In another aspect, the present invention provides a method of producing a hybrid toxin active against insects, comprising: (a) obtaining a transgenic host cell comprising a chimeric gene, which itself comprises a heterologous promoter sequence operatively linked to the nucleic acid molecule of the invention; and (b) expressing the nucleic acid molecule in the transgenic cell, which results in at least one hybrid toxin that is active against insects.

In a further aspect, the present invention provides a method of producing an insect-resistant transgenic plant, comprising introducing a nucleic acid molecule of the invention into the plant, wherein the nucleic acid molecule encodes a hybrid toxin and wherein the hybrid toxin is expressible in the transgenic plant in an effective amount to control an insect. According to one embodiment, the insects are lepidopteran insects, preferably selected from the group consisting of *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth).

In still a further aspect, the present invention provides a method of controlling an insect comprising delivering to the insects an effective amount of a hybrid toxin of the present invention. According to one embodiment, the insects are lepidopteran insects, preferably selected from the group consisting of *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth). Preferably the hybrid toxin is delivered to the insects orally. In one preferred embodiment, the hybrid toxin is delivered orally through a transgenic plant comprising a nucleic acid sequence that expresses a hybrid toxin of the present invention.

The present invention also provides a hybrid toxin active against insects, comprising a carboxy-terminal region of a Vip3 toxin joined in the amino to carboxy direction to an amino-terminal region of a different Vip3 toxin, wherein the carboxy-terminal region comprises an amino acid sequence which has at least 75% identity, preferably at least 85% identity, more preferably at least 95% identity, most preferably at least 99% identity with amino acids 661-788 of SEQ ID NO: 2; and wherein the amino-terminal region has at least 75% identity, preferably at least 85% identity, more preferably at least 95% identity, most preferably at least 99% identity with amino acids 1-660 of SEQ ID NO: 5. In a preferred embodiment, the carboxy-terminal region comprises amino acids 661-788 of SEQ ID NO: 2, and the amino-terminal region comprises amino acids 1-660 of SEQ ID NO: 5. In a most preferred embodiment, the hybrid toxin comprises amino acids 1-788 of SEQ ID NO: 11.

The hybrid toxin, according to this aspect of the invention, is preferably active against lepidopteran insects, more preferably against lepidopteran insects selected from the group consisting of *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth).

Also encompassed by this aspect of the invention is a nucleic acid molecule comprising a nucleotide sequence that encodes the hybrid toxin of this aspect.

The invention further provides a method of controlling insects wherein a transgenic plant comprising a hybrid toxin of the invention further comprises a second nucleic acid sequence or groups of nucleic acid sequences that encode a second pesticidal principle. Particularly preferred second nucleic acid sequences are those that encode a δ-endotoxin, those that encode another Vegetative Insecticidal Protein toxin or those that encode a pathway for the production of a non-proteinaceous pesticidal principle.

Yet another aspect of the present invention is the provision of a method for mutagenizing a nucleic acid molecule according to the present invention, wherein the nucleic acid molecule has been cleaved into populations of double-stranded random fragments of a desired size, comprising: (a) adding to the population of double-stranded random fragments one or more single- or double-stranded oligonucleotides, wherein the oligonucleotides each comprise an area of identity and an area of heterology to a double-stranded template polynucleotide; (b) denaturing the resultant mixture of double-stranded random fragments and oligonucleotides into single-stranded fragments; (c) incubating the resultant population of single-stranded fragments with polymerase under conditions which result in the annealing of the single-stranded fragments at the areas of identity to form pairs of annealed fragments, the areas of identity being sufficient for one member of the pair to prime replication of the other, thereby forming a mutagenized double-stranded polynucleotide; and (d) repeating the second and third steps for at least two further cycles, wherein the resultant mixture in the second step of a further cycle includes the mutagenized double-stranded polynucleotide from the third step of the previous cycle, and wherein the further cycle forms a further mutagenized double-stranded polynucleotide.

Other aspects and advantages of the present invention will become apparent to those skilled in the art from a study of the following description of the invention and non-limiting examples.

BRIEF DESCRIPTION OF THE SEQUENCES IN THE SEQUENCE LISTING

SEQ ID NO: 1 is a native vip3C nucleotide sequence.

SEQ ID NO: 2 is the amino acid sequence encoded by SEQ ID NO: 1.

SEQ ID NO: 3 is a maize optimized vip3C nucleotide sequence.

SEQ ID NO: 4 is a native vip3A(a) nucleotide sequence.

SEQ ID NO: 5 is the amino acid sequence encoded by SEQ ID NO: 5.

SEQ ID NO: 6 is a native vip3B nucleotide sequence.

SEQ ID NO: 7 is the amino acid sequence encoded by SEQ ID NO: 7.

SEQ ID NO: 8 is a native vip3Z nucleotide sequence.

SEQ ID NO: 9 is the amino acid sequence encoded by SEQ ID NO: 9.

SEQ ID NO: 10 is a hybrid vip3A-C nucleotide sequence.

SEQ ID NO: 11 is the amino acid sequence encoded by SEQ ID NO: 10.

SEQ ID NO: 12-29 are primer sequences useful in practicing the invention.

SEQ ID NO: 30 is the nucleotide sequence of the vector pNOV2149.

SEQ ID NO: 31 is the vip3C-12168 nucleotide sequence.

SEQ ID NO: 32 is the amino acid sequence encoded by SEQ ID NO: 31.

SEQ ID NO: 33 is the maize optimized vip3C-12168 nucleotide sequence.

DEPOSITS

The following material was deposited with the Agricultural Research Service, Patent Culture Collection (NRRL), 1815 North University Street, Peoria, Ill. 61604, under the terms of the Budapest Treaty on the International Recognition of the Deposit of Microorganisms for the Purposes of Patent Procedure. All restrictions on the availability of the deposited material will be irrevocably removed upon granting of the patent.

| Isolate/Clone | Accession Number | Date of Deposit |
|---|---|---|
| B.t. strain C1674 | NRRL B-30556 | Feb. 7, 2002 |
| B.t. strain C536 | NRRL B-30557 | Feb. 7, 2002 |
| *E. coli* BL21 (pNOV3906) | NRRL B-30555 | Feb. 7, 2002 |
| *E. coli* BL21 (pNOV3905) | NRRL B-30554 | Feb. 7, 2002 |
| *E. coli* DH5α (pNOV3910) | NRRL B-30553 | Feb. 7, 2002 |
| *E. coli* DH5α (pNOV3911) | NRRL B-30552 | Feb. 7, 2002 |
| *E. coli* DH5α (pNOV3912) | NRRL B-30551 | Feb. 7, 2002 |

DEFINITIONS

"Activity" of the toxins of the invention is meant that the toxins function as orally active insect control agents, have a toxic effect, or are able to disrupt or deter insect feeding, which may or may not cause death of the insect. When a toxin of the invention is delivered to the insect, the result is typically death of the insect, or the insect does not feed upon the source that makes the toxin available to the insect.

"Associated with/operatively linked" refer to two nucleic acid sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

A "chimeric gene" is a recombinant nucleic acid sequence in which a promoter or regulatory nucleic acid sequence is operatively linked to, or associated with, a nucleic acid sequence that codes for an mRNA or which is expressed as a protein, such that the regulator nucleic acid sequence is able to regulate transcription or expression of the associated nucleic acid sequence. The regulator nucleic acid sequence of the chimeric gene is not normally operatively linked to the associated nucleic acid sequence as found in nature.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

To "control" insects means to inhibit, through a toxic effect, the ability of insect pests to survive, grow, feed, and/or reproduce, or to limit insect-related damage or loss in crop plants. To "control" insects may or may not mean killing the insects, although it preferably means killing the insects.

Corresponding to: in the context of the present invention, "corresponding to" or "corresponds to" means that when the nucleic acid coding sequences or amino acid sequences of different Vip3 genes or proteins are aligned with each other, the nucleic or amino acids that "correspond to" certain enumerated positions are those that align with these positions but that are not necessarily in these exact numerical positions relative to the particular Vip3's respective nucleic acid coding sequence or amino acid sequence. Likewise, when the coding or amino acid sequence of a particular Vip3 (for example, Vip3Z) is aligned with the coding or amino acid sequence of a reference Vip3 (for example, Vip3C), the nucleic acids or amino acids in the Vip3Z sequence that "correspond to" certain enumerated positions of the Vip3C sequence are those that align with these positions of the Vip3C sequence, but are not necessarily in these exact numerical positions of the Vip3Z protein's respective nucleic acid coding sequence or amino acid sequence.

To "deliver" a toxin means that the toxin comes in contact with an insect, resulting in toxic effect and control of the insect. The toxin can be delivered in many recognized ways, e.g., orally by ingestion by the insect or by contact with the insect via transgenic plant expression, formulated protein composition(s), sprayable protein composition(s), a bait matrix, or any other art-recognized toxin delivery system.

"Effective insect-controlling amount" means that concentration of toxin that inhibits, through a toxic effect, the ability of insects to survive, grow, feed and/or reproduce, or to limit insect-related damage or loss in crop plants. "Effective insect-controlling amount" may or may not mean killing the insects, although it preferably means killing the insects.

"Expression cassette" as used herein means a nucleic acid sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

A "heterologous" nucleic acid sequence is a nucleic acid sequence not naturally associated with a host cell into which it is introduced, including non-naturally occurring multiple copies of a naturally occurring nucleic acid sequence.

A "homologous" nucleic acid sequence is a nucleic acid sequence naturally associated with a host cell into which it is introduced.

"Homologous recombination" is the reciprocal exchange of nucleic acid fragments between homologous nucleic acid molecules.

"Hybrid toxin" as used herein is an insecticidal toxin made by the hand of man which comprises amino acid regions or fragments of one toxin joined with amino acid regions or fragments from a different toxin. For example, without limitation, joining the C-terminal region of Vip3C, from amino acids 661-788 of SEQ ID NO: 2, with the N-terminal region of Vip3A, from amino acid 1-660 of SEQ ID NO: 4, creates a hybrid toxin with an amino acid sequence set forth in SEQ ID NO: 11.

"Insecticidal" is defined as a toxic biological activity capable of controlling insects, preferably by killing them.

A nucleic acid sequence is "isocoding with" a reference nucleic acid sequence when the nucleic acid sequence encodes a polypeptide having the same amino acid sequence as the polypeptide encoded by the reference nucleic acid sequence.

An "isolated" nucleic acid molecule or an isolated protein or toxin is a nucleic acid molecule or protein or toxin that, by the hand of man, exists apart from its native environment and is therefore not a product of nature. An isolated nucleic acid molecule or protein or toxin may exist in a purified form or may exist in a non-native environment such as, for example, a recombinant host cell or a transgenic plant.

Native: refers to a gene that is present in the genome of an untransformed cell.

Naturally occurring: the term "naturally occurring" is used to describe an object that can be found in nature as distinct from being artificially produced by man. For example, a protein or nucleotide sequence present in an organism (including a virus), which can be isolated from a source in nature and which has not been intentionally modified by man in the laboratory, is naturally occurring.

A "nucleic acid molecule" or "nucleic acid sequence" is a linear segment of single- or double-stranded DNA or RNA that can be isolated from any source. In the context of the present invention, the nucleic acid molecule is preferably a segment of DNA.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "promoter" is an untranslated DNA sequence upstream of the coding region that contains the binding site for RNA polymerase 11 and initiates transcription of the DNA. The promoter region may also include other elements that act as regulators of gene expression.

A "protoplast" is an isolated plant cell without a cell wall or with only parts of the cell wall.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

A "shuffled" nucleic acid is a nucleic acid produced by a shuffling procedure such as any shuffling procedure set forth herein. Shuffled nucleic acids are produced by recombining (physically or virtually) two or more nucleic acids (or character strings), e.g., in an artificial, and optionally recursive, fashion. Generally, one or more screening steps are used in shuffling processes to identify nucleic acids of interest; this screening step can be performed before or after any recombination step. In some (but not all) shuffling embodiments, it is desirable to perform multiple rounds of recombination prior to selection to increase the diversity of the pool to be screened. The overall process of recombination and selection are optionally repeated recursively. Depending on context, shuffling can refer to an overall process of recombination and selection, or, alternately, can simply refer to the recombinational portions of the overall process.

Substantially identical: the phrase "substantially identical," in the context of two nucleic acid or protein sequences, refers to two or more sequences or subsequences that have at least 60%, preferably 80%, more preferably 90, even more preferably 95%, and most preferably at least 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In an especially preferred embodiment, the sequences are substantially identical over the entire length of the coding regions. Furthermore, substantially identical nucleic acid or protein sequences perform substantially the same function.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., *J.*

*Mol. Biol.* 215: 403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology-Hybridization with Nucleic* Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2× SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1× SSC at 45° C. for 15 minutes. An example low stringency wash for a duplex of, e.g., more than 100 nucleotides, is 4-6× SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2× SSC, 0.1% SDS at 50° C., more desirably in 7% sodium dodecyl sulfate (SDS), 0.5 M $NaPO_4$, 1 mM EDTA at 50° C. with washing in 1× SSC, 0.1% SDS at 50° C., more desirably still in 7% sodium dodecyl sulfate (SDS), 0.5 M $NaPO_4$, 1 mM EDTA at 50° C. with washing in 0.5× SSC, 0.1% SDS at 50° C., preferably in 7% sodium dodecyl sulfate (SDS), 0.5 M $NaPO_4$, 1 mM EDTA at 50° C. with washing in 0.1× SSC, 0.1% SDS at 50° C., more preferably in 7% sodium dodecyl sulfate (SDS), 0.5 M $NaPO_4$, 1 mM EDTA at 50° C. with washing in 0.1× SSC, 0.1% SDS at 65° C.

A further indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

"Synthetic" refers to a nucleotide sequence comprising structural characters that are not present in the natural sequence. For example, an artificial sequence that resembles more closely the G+C content and the normal codon distribution of dicot and/or monocot genes is said to be synthetic.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

The "Vip3 class of proteins" comprises Vip3A(a), Vip3A(b), Vip3A(c), Vip3B, Vip3C(a), Vip3C(b), Vip3Z, and their homologues. "Homologue" is used throughout to mean that the indicated protein or polypeptide bears a defined relationship to other members of the Vip3 class of proteins. This defined relationship includes but is not limited to, 1) proteins which are at least 70%, more preferably at least 80% and most preferably at least 90% identical at the sequence level to another member of the Vip3 class of proteins while also retaining pesticidal activity, 2) proteins which are cross-reactive to antibodies which immunologically recognize another member of the Vip3 class of proteins, 3) proteins which are cross-reactive with a receptor to another member of the Vip3 class of proteins and retain the ability to induce programmed cell death, and 4) proteins which are at least 70%, more preferably at least 80% and most preferably at least 90% identical at the sequence level to the toxic core region of another member of the Vip3 class of proteins while also retaining pesticidal activity. Other Vip3 homologues have been disclosed in WO 98/18932, WO 98/33991, WO 98/00546, and WO 99/57282.

Nucleotides are indicated by their bases by the following standard abbreviations: adenine (A), cytosine (C), thymine (T), and guanine (G). Amino acids are likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

DETAILED DESCRIPTION OF THE INVENTION

This invention relates to nucleic acid sequences whose expression results in novel toxins, and to the making and using of the toxins to control insect pests. The nucleic acid sequences are derived from *Bacillus*, a gram-positive spore-forming microorganism. In particular, novel Vip3 proteins, useful as pesticidal agents, are provided.

For purposes of the present invention, insect pests include insects selected from, for example, the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, and Trichoptera, particularly Lepidoptera.

Tables 1-7 give a list of pests associated with major crop plants. Such pests are included within the scope of the present invention.

TABLE 1

| Lepidoptera |
|---|
| *Ostrinia nubilalis*, European corn borer |
| *Agrotis ipsilon*, black cutworm |
| *Helicoverpa zea*, corn earworm |
| *Spodoptera frugiperda*, fall armyworm |
| *Diatraea grandiosella*, southwestern corn borer |
| *Elasmopalpus lignosellus*, lesser cornstalk borer |
| *Diatraea saccharalis*, sugarcane borer |
| *Heliohtis virescens*, cotton bollworm |
| *Scirpophaga incertulas*, yellow stemborer |
| *Chilo polychrysa*, darkheaded riceborer |
| *Mythimna separata*, oriental armyworm |
| *Chilo partellus*, sorghum borer |
| *Feltia subterranea*, granulate cutworm |
| *Homoeosoma electellum*, sunflower head moth |
| *Spodoptera exigua*, beet armyworm |
| *Pectinophora gossypiella*, pink bollworm |
| *Scirpophaga innotata*, white stemborer |
| *Cnaphalocrocis medinalis*, leaffolder |
| *Chilo plejadellus*, rice stalk borer |
| *Nymphula depunctalis*, caseworm |
| *Spodoptera litura*, cutworm |
| *Spodoptera mauritia*, rice swarming caterpillar |
| *Cochylis hospes*, banded sunflower moth |
| *Pseudaletia unipunctata*, army worm |
| *Agrotis orthogonia*, pale western cutworm |
| *Pseudoplusia includens*, soybean looper |
| *Anticarsia gemmatalis*, velvetbean caterpillar |
| *Plathypena scabra*, green cloverworm |

TABLE 2

| Coleoptera |
|---|
| *Diabrotica virgifera*, western corn rootworm |
| *Diabrotica longicornis*, northern corn rootworm |
| *Diabrotica undecimpunctata*, southern corn rootworm |
| *Cyclocephala borealis*, northern masked chafer (white grub) |
| *Cyclocephala immaculata*, southern masked chafer (white grub) |
| *Popillia japonica*, Japanese beetle |
| *Chaetocnema pulicaria*, corn flea beetle |
| *Sphenophorus maidis*, maize billbug |
| *Phyllophaga crinita*, white grub |
| *Melanotus* spp., *Eleodes*, *Conoderus*, and *Aeolus* spp., wireworms |
| *Oulema melanopus*, cereal leaf beetle |
| *Chaetocnema pulicaria*, corn flea beetle |
| *Oulema melanopus*, cereal leaf beetle |
| *Hypera punctata*, clover leaf weevil |
| *Anthonomus grandis*, boll weevil |
| *Colaspis brunnea*, grape colaspis |
| *Lissorhoptrus oryzophilus*, rice water weevil |
| *Sitophilus oryzae*, rice weevil |
| *Epilachna varivestis*, Mexican bean beetle |

TABLE 3

| Homoptera |
|---|
| *Rhopalosiphum maidis*, corn leaf aphid |
| *Anuraphis maidiradicis*, corn root aphid |
| *Sipha flava*, yellow sugarcane aphid |
| *Schizaphis graminum*, greenbug |
| *Macrosiphum avenae*, English grain aphid |
| *Aphis gossypii*, cotton aphid |
| *Pseudatomoscelis seriatus*, cotton fleahopper |
| *Trialeurodes abutilonea*, bandedwinged whitefly |
| *Nephotettix nigropictus*, rice leafhopper |
| *Myzus persicae*, green peach aphid |
| *Empoasca fabae*, potato leafhopper |

TABLE 4

| Hemiptera |
| --- |
| *Blissus leucopterus leucopterus*, chinch bug |
| *Lygus lineolaris*, tarnished plant bug |
| *Acrosternum hilare*, green stink bug |
| *Euschistus servus*, brown stink bug |

TABLE 5

| Orthroptera |
| --- |
| *Melanoplus femurrubrum*, redlegged grasshopper |
| *Melanoplus sanguinipes*, migratory grasshopper |
| *Melanoplus differentialis*, differential grasshopper |

TABLE 6

| Diptera |
| --- |
| *Hylemya platura*, seedcorn maggot |
| *Agromyza parvicornis*, corn blotch leafminer |
| *Contarinia sorghicola*, sorghum midge |
| *Mayetiola destructor*, Hessian fly |
| *Sitodiplosis mosellana*, wheat midge |
| *Meromyza americana*, wheat stem maggot |
| *Hylemya coarctata*, wheat bulb fly |
| *Neolasioptera murtfeldtiana*, sunflower seed midge |

TABLE 7

| Thysanoptera |
| --- |
| *Anaphothrips obscurus*, grass thrips |
| *Frankliniella fusca*, tobacco thrips |
| *Thrips tabaci*, onion thrips |
| *Sericothrips variabilis*, soybean thrips |

The expression of the nucleic acid sequences of the present invention results in toxins that can be used to control lepidopteran insects, for example, without limitation, *Ostrinia nubilalis* (European corn borer), *Plutella xylostella* (diamondback moth), *Spodoptera frugiperda* (fall armyworm), *Agrotis epsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth).

In one preferred embodiment, the invention encompasses an isolated nucleic acid molecule comprising a nucleotide sequence that: (a) has a compliment that hybridizes to nucleotides 1981-2367 of SEQ ID NO: 1 in 7% sodium dodecyl sulfate (SDS), 0.5 M $NaPO_4$, 1 mM EDTA at 50° C. with washing in 0.1× SSC, 0.1% SDS at 65° C.; or (b) is isocoding with the nucleotide sequence of (a); or (c) comprises a consecutive 20 base pair nucleotide portion identical in sequence to a consecutive 20 base pair nucleotide portion of a nucleotide sequence of (a) or (b); or (d) has at least 93% sequence identity with SEQ ID NO: 1; or (e) encodes an amino acid sequence having at least 91% sequence identity with SEQ ID NO: 2, wherein expression of the isolated nucleic acid molecule results in insect control activity. When expressed in a heterologous host, the nucleic acid molecule of SEQ ID NO: 1, SEQ ID NO: 3, SEQ ID NO: 10, and SEQ ID NO: 31 results in insect control activity against *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth), showing that the nucleotide sequence set forth in SEQ ID NO: 1, SEQ ID NO: 3, SEQ ID NO: 10, and SEQ ID NO: 31 is sufficient for such insect control activity.

In one embodiment, the invention encompasses a nucleic acid molecule comprising a nucleotide sequence that has at least 75% sequence identity with nucleotides 1981-2367 of SEQ ID NO: 1. Preferably, the isolated nucleic acid molecule comprises a nucleotide sequence that has at least 85% sequence identity with nucleotides 1981-2367 of SEQ ID NO: 1. More preferably, the isolated nucleic acid molecule comprises a nucleotide sequence that has at least 95% sequence identity with nucleotides 1981-2367 of SEQ ID NO: 1. Even more preferably, the isolated nucleic acid molecule comprises a nucleotide sequence that has at least 99% sequence identity with nucleotides 1981-2367 of SEQ ID NO: 1. Most preferably, the isolated nucleic acid molecule comprises nucleotides 1981-2367 of SEQ ID NO: 1 or SEQ ID NO: 3.

In another embodiment, the invention encompasses a nucleic acid molecule comprising a nucleotide sequence that has at least 93% sequence identity with SEQ ID NO: 1. Preferably, the isolated nucleic acid molecule comprises a nucleotide sequence that has at least 95% sequence identity with SEQ ID NO: 1. More preferably, the isolated nucleic acid molecule comprises a nucleotide sequence that has at least 99% sequence identity with SEQ ID NO: 1. Most preferably, the isolated nucleic acid molecule comprises nucleotides 1-2367 of a nucleotide sequence selected from the group consisting of SEQ ID NO: 1, SEQ ID NO: 3, SEQ ID NO: 10, SEQ ID NO: 31, and SEQ ID NO: 33.

In yet another embodiment, the invention encompasses a nucleic acid molecule comprised in a *Bacillus thuringiensis* isolate selected from the group consisting of C1674, designated NRRL accession B-30556; and C536, designated NRRL accession B-30557. In a preferred embodiment, the invention encompasses a nucleic acid molecule comprised in an *E. coli* clone selected from the group consisting of pNOV3910, designated NRRL accession B-30553; pNOV3911, designated NRRL accession B-30552; pNOV3906, designated NRRL accession B-30555; pNOV3905, designated NRRL accession B-30554; and pNOV3912, designated NRRL accession B-30551, whose expression results in an insecticidal toxin.

The present invention also encompasses an isolated nucleic acid molecule which encodes a toxin comprising an amino acid sequence with at least 75% identity with amino acids 661-788 of the amino acid sequence of SEQ ID NO: 2. Preferably, the isolated nucleic acid molecule encodes a toxin comprising an amino acid sequence which has at least 85% identity with amino acids 661-788 of the amino acid sequence of SEQ ID NO: 2. More preferably, the isolated nucleic acid molecule encodes a toxin comprising an amino acid sequence which has at least 95% identity with amino acids 661-788 of the amino acid sequence of SEQ ID NO: 2. Even more preferably, the isolated nucleic acid molecule encodes a toxin comprising an amino acid sequence which has at least 99% identity with amino acids 661-788 of the amino acid sequence of SEQ ID NO: 2. Most preferably, the isolated nucleic acid molecule encodes a toxin comprising amino acids 661-788 of the amino acid sequence of SEQ ID NO: 2.

In another embodiment, the isolated nucleic acid molecule encodes a toxin comprising an amino acid sequence which has 91% identity to the amino acid sequence set forth in SEQ ID NO: 2. Preferably, the isolated nucleic acid molecule encodes a toxin comprising an amino acid sequence which has 95% identity to the amino acid sequence set forth in SEQ ID NO: 2. More preferably, the isolated nucleic acid molecule encodes a toxin comprising an amino acid sequence which has 99% identity to the amino acid sequence set forth in SEQ ID NO: 2. Most preferably, the isolated nucleic acid molecule encodes a toxin comprising the amino acid sequence set forth in SEQ ID NO: 2, SEQ ID NO: 11, or SEQ ID NO: 32.

The present invention also encompasses recombinant vectors comprising the nucleic acid sequences of this invention. In such vectors, the nucleic acid sequences are preferably comprised in expression cassettes comprising regulatory elements for expression of the nucleotide sequences in a transgenic host cell capable of expressing the nucleotide sequences. Such regulatory elements usually comprise promoter and termination signals and preferably also comprise elements allowing efficient translation of polypeptides encoded by the nucleic acid sequences of the present invention. Vectors comprising the nucleic acid sequences are usually capable of replication in particular host cells, preferably as extrachromosomal molecules, and are therefore used to amplify the nucleic acid sequences of this invention in the host cells. In one embodiment, host cells for such vectors are microorganisms, such as bacteria, in particular *E. coli*. In another embodiment, host cells for such recombinant vectors are endophytes or epiphytes. A preferred host cell for such vectors is a eukaryotic cell, such as a yeast cell, a plant cell, or an insect cell. Plant cells such as maize cells or cotton are most preferred host cells. In another preferred embodiment, such vectors are viral vectors and are used for replication of the nucleotide sequences in particular host cells, e.g. insect cells or plant cells. Recombinant vectors are also used for transformation of the nucleotide sequences of this invention into transgenic host cells, whereby the nucleotide sequences are stably integrated into the DNA of such transgenic host cells. In one, such transgenic host cells are prokaryotic cells. In a preferred embodiment, such transgenic host cells are eukaryotic cells, such as yeast cells, insect cells, or plant cells. In a most preferred embodiment, the transgenic host cells are plant cells, such as maize cells or cotton cells.

In yet another aspect, the present invention provides toxins produced by the expression of the nucleic acid molecules of the present invention.

In preferred embodiments, the insecticidal toxins of the invention comprise a polypeptide encoded by a nucleotide sequence of the invention. In a further preferred embodiment, the toxin is produced by a *Bacillus thuringiensis* isolated selected from the group consisting of C1674, designated NRRL accession B-30556; and C536, designated NRRL accession B-30557.

In another embodiment, the toxins are produced by an *E. coli* clone selected from the group consisting of pNOV3910, designated NRRL accession B-30553; pNOV3911, designated NRRL accession B-30552; pNOV3906, designated NRRL accession B-30555; pNOV3905, designated NRRL accession B-30554; and pNOV3912, designated NRRL accession B-30551. In a preferred embodiment, the toxin is produced by the expression of the nucleic acid molecule comprising nucleotides 1-2367 of SEQ ID NO: 1 or nucleotides 1-2367 of SEQ ID NO: 3, or nucleotides 1-2367 of SEQ ID NO: 10, or nucleotides 1-2367 of SEQ ID NO: 31.

The present invention encompasses a toxin which comprises an amino acid sequence which has at least 75% identity with amino acids 661-788 of the amino acid sequence of SEQ ID NO: 2. Preferably, the toxin comprises an amino acid sequence which has at least 85% identity with amino acids 661-788 of the amino acid sequence of SEQ ID NO: 2. Even more preferably, the toxin comprises an amino acid sequence which has at least 95% identity with amino acids 661-788 of the amino acid sequence of SEQ ID NO: 2. Even more preferably, the toxin comprises an amino acid sequence which has at least 99% identity with amino acids 661-788 of the amino acid sequence of SEQ ID NO: 2. Most preferably, the toxin comprises amino acids 661-788 of SEQ ID NO: 2.

In another preferred embodiment, a toxin of the present invention comprises an amino acid sequence which has at least 91% identity with the amino acid sequence set forth in SEQ ID NO: 2. Preferably, the toxin comprises an amino acid sequence which has at least 95% identity with the amino acid sequence set forth in SEQ ID NO: 2. More preferably, the toxin comprises an amino acid sequence which has at least 99% identity with the amino acid sequence set forth in SEQ ID NO: 2. Most preferably, the toxin comprises the amino acid sequence set forth in SEQ ID NO: 2, SEQ ID NO: 11, or SEQ ID NO: 32.

The toxins of the present invention have insect control activity when tested against insect pests in bioassays. In another preferred embodiment, the toxins of the invention are active against lepidopteran insects, preferably against *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth). The insect controlling properties of the insecticidal toxins of the invention are further illustrated in Examples 6, 8, 9 and 13.

The present invention also encompasses hybrid toxins which are active against insects, wherein the hybrid toxins are encoded by nucleic acid molecules comprising a nucleotide sequence that: (a) has a compliment that hybridizes to nucleotides 1981-2367 of SEQ ID NO: 1 in 7% sodium dodecyl sulfate (SDS), 0.5 M $NaPO_4$, 1 mM EDTA at 50° C. with washing in 0.1× SSC, 0.1% SDS at 65° C.; or (b) is isocoding with the nucleotide sequence of (a); or (c) comprises a consecutive 20 base pair nucleotide portion identical in sequence to a consecutive 20 base pair nucleotide portion of a nucleotide sequence of (a) or (b), wherein expression of the nucleic acid molecule results in insect control activity. In a preferred embodiment, the hybrid toxin is encoded by the approximately 2.4 kb DNA fragment comprised in pNOV3912, deposited in the *E. coli* strain DH5α designated NRRL accession B-30551, whose expression results in an insecticidal hybrid toxin. Specifically exemplified herein is a hybrid toxin that is encoded by the nucleotide sequence set forth in SEQ ID NO: 10. When expressed in a heterologous host, the nucleic acid molecule of SEQ ID NO: 10 results in insect control activity against *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth). The insect controlling properties of the exemplified hybrid toxin of the invention is further illustrated in Example 9.

The present invention also encompasses hybrid toxins active against insects that comprise a carboxy-terminal region of a Vip3 toxin joined in the amino to carboxy direction to an amino-terminal region of a different Vip3 toxin, wherein the carboxy-terminal region comprises an amino acid sequence which has at least 75% identity, preferably at least 85% identity, more preferably at least 95% identity, most preferably at least 99% identity, with amino acids 661-788 of SEQ ID NO: 2; and wherein the amino-terminal region has at least 75% identity, preferably at least 85% identity, more preferably at least 95% identity, most preferably at least 99% identity, with amino acids 1-660 of SEQ ID NO: 5. In a preferred embodiment, the carboxy-terminal region comprises amino acids 661-788 of SEQ ID NO: 2, and the amino-terminal region comprises amino acids 1-660 of SEQ ID NO: 65 In a more preferred embodiment, the hybrid toxin comprises amino acids 1-788 of SEQ ID NO: 11.

In further embodiments, the nucleotide sequences of the invention can be modified by incorporation of random mutations in a technique known as in vitro recombination or DNA shuffling. This technique is described in Stemmer et al., Nature 370:389-391 (1994) and U.S. Pat. No. 5,605,793, which are incorporated herein by reference. Millions of mutant copies of a nucleotide sequence are produced based on an original nucleotide sequence of this invention and variants with improved properties, such as increased insecticidal activity, enhanced stability, or different specificity or range of target insect pests are recovered. The method encompasses forming a mutagenized double-stranded polynucleotide from a template double-stranded polynucleotide comprising a nucleotide sequence of this invention, wherein the template double-stranded polynucleotide has been cleaved into double-stranded-random fragments of a desired size, and comprises the steps of adding to the resultant population of double-stranded random fragments one or more single or double-stranded oligonucleotides, wherein said oligonucleotides comprise an area of identity and an area of heterology to the double-stranded template polynucleotide; denaturing the resultant mixture of double-stranded random fragments and oligonucleotides into single-stranded fragments; incubating the resultant population of single-stranded fragments with a polymerase under conditions which result in the annealing of said single-stranded fragments at said areas of identity to form pairs of annealed fragments, said areas of identity being sufficient for one member of a pair to prime replication of the other, thereby forming a mutagenized double-stranded polynucleotide; and repeating the second and third steps for at least two further cycles, wherein the resultant mixture in the second step of a further cycle includes the mutagenized double-stranded polynucleotide from the third step of the previous cycle, and the further cycle forms a further mutagenized double-stranded polynucleotide. In a preferred embodiment, the concentration of a single species of double-stranded random fragment in the population of double-stranded random fragments is less than 1% by weight of the total DNA. In a further preferred embodiment, the template double-stranded polynucleotide comprises at least about 100 species of polynucleotides. In another preferred embodiment, the size of the double-stranded random fragments is from about 5 bp to 5 kb. In a further preferred embodiment, the fourth step of the method comprises repeating the second and the third steps for at least 10 cycles.

Expression of the Nucleotide Sequences in Heterologous Microbial Hosts

As biological insect control agents, the insecticidal toxins are produced by expression of the nucleotide sequences in heterologous host cells capable of expressing the nucleotide sequences. In a first embodiment, *B. thuringiensis* cells comprising modifications of a nucleotide sequence of this invention are made. Such modifications encompass mutations or deletions of existing regulatory elements, thus leading to altered expression of the nucleotide sequence, or the incorporation of new regulatory elements controlling the expression of the nucleotide sequence. In another embodiment, additional copies of one or more of the nucleotide sequences are added to *Bacillus thuringiensis* cells either by insertion into the chromosome or by introduction of extrachromosomally replicating molecules containing the nucleotide sequences.

In another embodiment, at least one of the nucleotide sequences of the invention is inserted into an appropriate expression cassette, comprising a promoter and termination signals. Expression of the nucleotide sequence is constitutive, or an inducible promoter responding to various types of stimuli to initiate transcription is used. In a preferred embodiment, the cell in which the toxin is expressed is a microorganism, such as a virus, a bacteria, or a fungus. In a preferred embodiment, a virus, such as a baculovirus, contains a nucleotide sequence of the invention in its genome and expresses large amounts of the corresponding insecticidal toxin after infection of appropriate eukaryotic cells that are suitable for virus replication and expression of the nucleotide sequence. The insecticidal toxin thus produced is used as an insecticidal agent. Alternatively, baculoviruses engineered to include the nucleotide sequence are used to infect insects in vivo and kill them either by expression of the insecticidal toxin or by a combination of viral infection and expression of the insecticidal toxin.

Bacterial cells are also hosts for the expression of the nucleotide sequences of the invention. In a preferred embodiment, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera *Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces* and *Xanthomonas*. Symbiotic fungi, such as *Trichoderma* and *Gliocladium* are also possible hosts for expression of the inventive nucleotide sequences for the same purpose.

Techniques for these genetic manipulations are specific for the different available hosts and are known in the art. For example, the expression vectors pKK223-3 and pKK223-2 can be used to express heterologous genes in *E. coli*, either in transcriptional or translational fusion, behind the tac or trc promoter. For the expression of operons encoding multiple ORFs, the simplest procedure is to insert the operon into a vector such as pKK223-3 in transcriptional fusion, allowing the cognate ribosome binding site of the heterologous genes to be used. Techniques for overexpression in gram-positive species such as *Bacillus* are also known in the art and can be used in the context of this invention (Quax et al. In:Industrial Microorganisms:Basic and Applied Molecular Genetics, Eds. Baltz et al., American Society for Microbiology, Washington (1993)). Alternate systems for overexpression rely for example, on yeast vectors and include the use of *Pichia, Saccharomyces* and *Kluyveromyces* (Sreekrishna, In:Industrial microorganisms:basic and applied molecular genetics, Baltz, Hegeman, and Skatrud eds., American Society for Microbiology, Washington (1993); Dequin & Barre, Biotechnology L2:173-177 (1994); van den Berg et al., Biotechnology 8:135-139 (1990)).

Plant Transformation

In a particularly preferred embodiment, at least one of the insecticidal toxins of the invention is expressed in a higher organism, e.g., a plant. In this case, transgenic plants expressing effective amounts of the toxins protect themselves from insect pests. When the insect starts feeding on such a transgenic plant, it also ingests the expressed toxins. This will deter the insect from further biting into the plant tissue or may even harm or kill the insect. A nucleotide sequence of the present invention is inserted into an expression cassette, which is then preferably stably integrated in the genome of said plant. In another preferred embodiment, the nucleotide sequence is included in a non-pathogenic self-replicating virus. Plants transformed in accordance with the present invention may be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar beet, sunflower, rapeseed, clover, tobacco, carrot, cotton, alfalfa, rice, potato, eggplant, cucumber, *Arabidopsis*, and woody plants such as coniferous and deciduous trees.

Once a desired nucleotide sequence has been transformed into a particular plant species, it may be propagated in that species or moved into other varieties of the same species, particularly including commercial varieties, using traditional breeding techniques.

A nucleotide sequence of this invention is preferably expressed in transgenic plants, thus causing the biosynthesis of the corresponding toxin in the transgenic plants. In this way, transgenic plants with enhanced resistance to insects are generated. For their expression in transgenic plants, the nucleotide sequences of the invention may require modification and optimization. Although in many cases genes from microbial organisms can be expressed in plants at high levels without modification, low expression in transgenic plants may result from microbial nucleotide sequences having codons that are not preferred in plants. It is known in the art that all organisms have specific preferences for codon usage, and the codons of the nucleotide sequences described in this invention can be changed to conform with plant preferences, while maintaining the amino acids encoded thereby. Furthermore, high expression in plants is best achieved from coding sequences that have at least about 35% GC content, preferably more than about 45%, more preferably more than about 50%, and most preferably more than about 60%. Microbial nucleotide sequences that have low GC contents may express poorly in plants due to the existence of ATTTA motifs that may destabilize messages, and AATAAA motifs that may cause inappropriate polyadenylation. Although preferred gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477-498 (1989)). In addition, the nucleotide sequences are screened for the existence of illegitimate splice sites that may cause message truncation. All changes required to be made within the nucleotide sequences such as those described above are made using well known techniques of site directed mutagenesis, PCR, and synthetic gene construction using the methods described in the published patent applications EP 0 385 962 (to Monsanto), EP 0 359 472 (to Lubrizol, and WO 93/07278 (to Ciba-Geigy).

In one embodiment of the invention synthetic genes are made according to the procedure disclosed in U.S. Pat. No. 5,625,136, herein incorporated by reference. In this procedure, maize preferred codons, i.e., the single codon that most frequently encodes that amino acid in maize, are used. The maize preferred codon for a particular amino acid can be derived, for example, from known gene sequences from maize. Maize codon usage for 28 genes from maize plants is found in Murray et al., Nucleic Acids Research 17:477-498 (1989), the disclosure of which is incorporated herein by reference. Specifically exemplified synthetic sequences of the present invention made with maize optimized codons are set forth in SEQ ID NO: 3 and SEQ ID NO: 33.

In this manner, the nucleotide sequences can be optimized for expression in any plant. It is recognized that all or any part of the gene sequence may be optimized or synthetic. That is, synthetic or partially optimized sequences may also be used.

For efficient initiation of translation, sequences adjacent to the initiating methionine may require modification. For example, they can be modified by the inclusion of sequences known to be effective in plants. Joshi has suggested an appropriate consensus for plants (NAR 15:6643-6653 (1987)) and Clonetech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (whilst leaving the second amino acid unmodified), or alternatively up to and including the GTC subsequent to the ATG (with the possibility of modifying the second amino acid of the transgene).

The novel vip3 toxin genes of the present invention, either as their native sequence or as optimized synthetic sequences as described above, can be operably fused to a variety of promoters for expression in plants including constitutive, inducible, temporally regulated, developmentally regulated, chemically regulated, tissue-preferred and tissue-specific promoters to prepare recombinant DNA molecules, i.e., chimeric genes. The choice of promoter will vary depending on the temporal and spatial requirements for expression, and also depending on the target species. Thus, expression of the nucleotide sequences of this invention in leaves, in stalks or stems, in ears, in inflorescences (e.g. spikes, panicles, cobs, etc.), in roots, and/or seedlings is preferred. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

Preferred constitutive promoters include the CaMV 35S and 19S promoters (Fraley et al., U.S. Pat. No. 5,352,605 issued Oct. 4, 1994). An additionally preferred promoter is derived from any one of several of the actin genes, which are expressed in most cell types. The promoter expression cassettes described by McElroy et al. (Mol. Gen. Genet. 231: 150-160 (1991)) can be easily modified for the expression of the novel toxin gene and are particularly suitable for use in monocotyledonous hosts.

Yet another preferred constitutive promoter is derived from ubiquitin, which is another gene product known to accumulate in many cell types. A ubiquitin promoter has been cloned from several species for use in transgenic plants, for example, sunflower (Binet et al., 1991. Plant Science 79: 87-94), maize (Christensen et al., 1989. Plant Molec. Biol. 12: 619-632), and *arabidopsis* (Norris et al. 1993. Plant Molec. Biol. 21:895-906). The maize ubiquitin promoter has been developed in transgenic monocot systems and its sequence and vectors constructed for monocot transformation are disclosed in the patent publication EP 0 342 926. The ubiquitin promoter is suitable for the expression of the novel toxin gene in transgenic plants, especially monocotyledons.

Tissue-specific or tissue-preferential promoters useful for the expression of the novel toxin genes of the invention in plants, particularly maize, are those that direct expression in root, pith, leaf or pollen. Such promoters are disclosed in WO 93/07278, herein incorporated by reference in its entirety. Other tissue specific promoters useful in the present invention include the cotton rubisco promoter disclosed in U.S. Pat. No. 6,040,504; the rice sucrose synthase promoter disclosed in U.S. Pat. No. 5,604,121; and the cestrum yellow leaf curling virus promoter disclosed in WO 01/73087, all incorporated by reference. Chemically inducible promoters useful for directing the expression of the novel toxin gene in plants are disclosed in U.S. Pat. No. 5,614,395 herein incorporated by reference in its entirety.

The nucleotide sequences of this invention can also be expressed under the regulation of promoters that are chemically regulated. This enables the Vip3 toxins to be synthesized only when the crop plants are treated with the inducing chemicals. Preferred technology for chemical induction of gene expression is detailed in the published application EP 0 332 104 (to Ciba-Geigy) and U.S. Pat. No. 5,614,395. A preferred promoter for chemical induction is the tobacco PR-1a promoter.

A preferred category of promoters is that which is wound inducible. Numerous promoters have been described which are expressed at wound sites and also at the sites of phytopathogen infection. Ideally, such a promoter should only be active locally at the sites of infection, and in this way the insecticidal toxins only accumulate in cells that need to synthesize the insecticidal toxins to kill the invading insect pest. Preferred promoters of this kind include those described by Stanford et al. Mol. Gen. Genet. 215:200-208 (1989), Xu et al. Plant Molec. Biol. 22:573-588 (1993), Logemann et al. Plant Cell 1:151-158 (1989), Rohrmeier & Lehle, Plant Molec. Biol. 22:783-792 (1993), Firek et al. Plant Molec. Biol. 22:129-142 (1993), and Warner et al. Plant J. 3:191-201 (1993).

Preferred tissue specific expression patterns include green tissue specific, root specific, stem specific, and flower specific. Promoters suitable for expression in green tissue include many that regulate genes involved in photosynthesis and many of these have been cloned from both monocotyledons and dicotyledons. A preferred promoter is the maize PEPC promoter from the phosphoenol carboxylase gene (Hudspeth & Grula, Plant Molec. Biol. 12:579-589 (1989)). A preferred promoter for root specific expression is that described by de Framond (FEBS 290:103-106 (1991); EP 0 452 269 to Ciba-Geigy). A preferred stem specific promoter is that described in U.S. Pat. No. 5,625,136 (to Ciba-Geigy) and which drives expression of the maize trpA gene.

Further preferred embodiments are transgenic plants expressing the nucleotide sequences in a wound-inducible or pathogen infection-inducible manner.

In addition to the selection of a suitable promoter, constructions for expression of an insecticidal toxin in plants require an appropriate transcription terminator to be attached downstream of the heterologous nucleotide sequence. Several such terminators are available and known in the art (e.g. tml from CaMV, E9 from rbcS). Any available terminator known to function in plants can be used in the context of this invention.

Numerous other sequences can be incorporated into expression cassettes described in this invention. These include sequences that have been shown to enhance expression such as intron sequences (e.g. from Adhl and bronzel) and viral leader sequences (e.g. from TMV, MCMV and AMV).

It may be preferable to target expression of the nucleotide sequences of the present invention to different cellular localizations in the plant. In some cases, localization in the cytosol may be desirable, whereas in other cases, localization in some subcellular organelle may be preferred. Subcellular localization of transgene-encoded enzymes is undertaken using techniques well known in the art. Typically, the DNA encoding the target peptide from a known organelle-targeted gene product is manipulated and fused upstream of the nucleotide sequence. Many such target sequences are known for the chloroplast and their functioning in heterologous constructions has been shown. The expression of the nucleotide sequences of the present invention is also targeted to the endoplasmic reticulum or to the vacuoles of the host cells. Techniques to achieve this are well known in the art.

Numerous transformation vectors available for plant transformation are known to those of ordinary skill in the plant transformation art, and the nucleic acid molecules of the invention can be used in conjunction with any such vectors. The selection of vector will depend upon the preferred transformation technique and the target plant species for transformation. For certain target species, different antibiotic or herbicide selection markers may be preferred. Selection markers used routinely in transformation include the nptII gene, which confers resistance to kanamycin and related antibiotics (Messing & Vierra., 1982. Gene 19: 259-268; and Bevan et al., 1983. Nature 304:184-187), the bar gene, which confers resistance to the herbicide phosphinothricin (White et al., 1990. Nucl. Acids Res 18: 1062, and Spencer et al., 1990. Theor. Appl. Genet 79: 625-631), the hph gene, which confers resistance to the antibiotic hygromycin (Blochinger & Diggelmann, Mol Cell Biol 4: 2929-2931), and the dhfr gene, which confers resistance to methatrexate (Bourouis et al., 1983. EMBO J. 2(7): 1099-1104), the EPSPS gene, which confers resistance to glyphosate (U.S. Pat. Nos. 4,940,935 and 5,188,642), and the mannose-6-phosphate isomerase gene, which provides the ability to metabolize mannose (U.S. Pat. Nos. 5,767,378 and 5,994,629). The choice of selectable marker is not, however, critical to the invention.

In another preferred embodiment, a nucleotide sequence of the present invention is directly transformed into the plastid genome. A major advantage of plastid transformation is that plastids are generally capable of expressing bacterial genes without substantial modification, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et aL (1994) Proc. Natl. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Natl. Acad. Sci. USA 87, 8526-8530; Staub, J. M., and Maliga, P. (1992) Plant Cell 4, 39-45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601-606). Substantial increases in transformation frequency are obtained by replacement of the recessive rRNA or r-protein antibiotic resistance genes with a dominant selectable marker, the bacterial aadA gene encoding the spectinomycin-cletoxifying enzyme aminoglycoside-3'-adenyltransf erase (Svab, Z., and Maliga, P. (1993) Proc. Natl. Acad. Sci. USA 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid-targeting vector and transformed into the plastid genome of a desired plant host. Plants homoplastic for plastid genomes containing a nucleotide sequence of the present invention are obtained, and are preferentially capable of high expression of the nucleotide sequence.

Combinations of Insect Control Principles

The pesticidal toxins of the invention can be used in combination with Bt δ-endotoxins or other pesticidal principles to increase pest target range. Furthermore, the use of the pesticidal toxins of the invention in combination with Bt δ-endotoxins or other pesticidal principles of a distinct nature has particular utility for the prevention and/or management of insect resistance.

The various insecticidal crystal proteins from *Bacillus thuringiensis* have been classified based upon their spectrum of activity and sequence similarity. The classification put forth by Hofte and Whiteley, Microbiol. Rev. 53: 242-255 (1989) placed the then known insecticidal crystal proteins into four major classes. Generally, the major classes are defined by the spectrum of activity, with the Cry1 proteins active against Lepidoptera, Cry2 proteins active against both Lepidoptera and Diptera, Cry3 proteins active against Coleoptera, and Cry4 proteins active against Diptera.

Within each major class, the δ-endotoxins are grouped according to sequence similarity. The Cry1 proteins are typically produced as 130-140 kDa protoxin proteins that are proteolytically cleaved to produce active toxins that are about 60-70 kDa. The active portion of the δ-endotoxin resides in the $NH_2$-terminal portion of the full-length molecule. Hofte and Whiteley, supra, classified the then known Cry1 proteins into six groups, 1Aa, 1Ab, 1Ac, 1B, 1C, and 1D. Since then, proteins classified as Cry1Ea, Cry1Fa, Cry9A, Cry9C and Cry9B, as well as others, have also been characterized.

The spectrum of insecticidal activity of an individual δ-endotoxin from *Bacillus thuringiensis* tends to be quite narrow, with a given δ-endotoxin being active against only a few insects. Specificity is the result of the efficiency of the various steps involved in producing an active toxin protein and its subsequent ability to interact with the epithelial cells in the insect digestive tract. In one preferred embodiment, expression of the nucleic acid molecules of the invention in transgenic plants is accompanied by the expression of one or more Bt δ-endotoxins. Particularly preferred Bt δ-endotoxins are those disclosed in U.S. Pat. No. 5,625,136, herein incorporated by reference.

It is well known that many δ-endotoxin proteins from *Bacillus thuringiensis* are actually expressed as protoxins. These protoxins are solubilized in the alkaline environment of the insect gut and are proteolytically converted by proteases into a toxic core fragment (Hofte and Whiteley, Microbiol. Rev. 53: 242-255 (1989)). For δ-endotoxin proteins of the Cry1 class, the toxic core fragment is localized in the N-terminal half of the protoxin. It is within the scope of the present invention that genes encoding either the full-length protoxin form or the truncated toxic core fragment of the novel toxin proteins can be used in plant transformation vectors to confer insecticidal properties upon the host plant.

Other insecticidal principles include protease inhibitors (both serine and cysteine types), lectins, α-amylase, peroxidase and cholesterol oxidase. Other Vip genes, such as vip1A (a) and vip2A(a) as disclosed in U.S. Pat. No. 5,849,870 and herein incorporated by reference, are also useful in the present invention.

This co-expression of more than one insecticidal principle in the same transgenic plant can be achieved by genetically engineering a plant to contain and express all the genes necessary. Alternatively, a plant, Parent 1, can be genetically engineered for the expression of genes of the present invention. A second plant, Parent 2, can be genetically engineered for the expression of a supplemental insect control principle. By crossing Parent 1 with Parent 2, progeny plants are obtained which express all the genes introduced into Parents 1 and 2.

The present invention further encompasses variants of the disclosed nucleic acid molecules. Naturally occurring variant sequences can be identified and/or isolated with the use of well-known molecular biology techniques, as, for example, with PCR and hybridization techniques as outlined below.

Variant vip3 nucleotide sequences include synthetically derived nucleotide sequences, such as those generated, for example, by using site-directed mutagenesis or those made by whole domain swaps, but which still exhibit pesticidal activity. Methods for mutagenesis and nucleotide sequence alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Generally, a nucleotide sequence of the invention will have at least 80%, preferably 85%, 90%, 95%, up to 98% or more sequence identity to its respective reference vip3 nucleotide sequence, and have pesticidal activity.

Variant vip3 nucleotide sequences also encompass sequences derived from a mutagenic and recombinogenic procedure such as DNA shuffling. With such a procedure, one or more different vip3 sequences of the present invention, for example, without limitation, vip3C(a), vip3C(b), vip3A-C, and vip3C-12168 can be recombined together or with other vip3 or related sequences, for example, and without limitation, vip3A (SEQ ID NO: 4), vip3B (SEQ ID NO: 6), and vip3Z (SEQ ID NO: 8), to create new vip3 nucleic acid molecules encoding Vip3 toxins possessing the desired properties. In this manner, libraries of recombinant vip3 polynucleotides are generated from a population of sequence related vip3 polynucleotides comprising sequence regions that have substantial sequence identity and can be homologously recombined in vitro or in vivo. Strategies for such DNA shuffling are known in the art. See, for example, Stemmer (1994) Proc. Natl. Acad. Sci. USA 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) Proc. Natl. Acad. Sci. USA 94:4504-4509; Crameri et al. (1998) Nature 391:288-291; International Patent Application WO 99/57128, and U.S. Pat. Nos. 5,605,793, 5,837,458 and 6,335,179.

Mutagenesis methods as disclosed herein can be combined with high-throughput, screening methods to detect the pesticidal activity of cloned, mutagenized Vip3 polypeptides in host cells. Mutagenized DNA molecules that encode active Vip3 polypeptides (e.g., secreted and detected by antibodies; or insecticidal in an insect bioassay) can be recovered from the host cells and rapidly sequenced using standard art procedures. These methods allow the rapid determination of the importance of individual amino acid residues in a Vip3 polypeptide of interest, and can be applied to polypeptides of unknown structure.

The libraries of recombinant vip3 genes that are produced using DNA shuffling methods are screened to identify those that exhibit improved properties for use in protecting plants against pests. Included among properties for which DNA shuffling is useful for obtaining improved vip3 pest resistance genes are increased potency against a target pest, increased target pest range, decreased susceptibility to development of resistance by pests, increased expression level, increased resistance to protease degradation, increased stability in environmental conditions, and reduced toxicity to a host plant. By using an appropriate screening strategy, one can simultaneously or sequentially obtain vip3 genes that are optimized for more than one property.

DNA shuffling is useful for obtaining vip3 pest resistance genes that encode toxins that exhibit enhanced potency against a target pest. Once the shuffling is completed, the resulting library of shuffled vip3 genes is screened to identify those that exhibit enhanced pesticidal activity. One way of performing this screening is to clone the protein-coding region of the shuffled vip3 genes into an expression vector that is suitable for expressing the genes in a chosen host cell such as, for example, *E. coli* or a crystal minus strain of *Bacillus thuringiensis*. One skilled in the art will recognize the advantages and disadvantages of using either of these two expression systems. For example, *Bacillus thuringiensis* would be more desirable in producing secreted Vip3 proteins. If desired, clones can be subjected to a preliminary screen, for example, by immunoassay, to identify those that produce a Vip3 protein of the correct size. Those that are positive in the preliminary screen are then tested in a functional screen to identify shuffled vip3 genes that encode a toxin having the desired enhanced activity.

A whole insect assay can be used for determining toxicity. In these assays, the Vip3 toxins expressed from the shuffled vip3 genes are placed on insect diet, for example, artificial diet or plant tissue, and consumed by the target insect. Those clones causing growth inhibition or mortality to the target insect can be tested in further bioassays to determine potency. Shuffled vip3 genes encoding toxins with enhanced potency can be identified as those that have a decreased $EC_{50}$ (concentration of toxin necessary to reduce insect growth by 50%) and/or $LC_{50}$ (concentration of toxin necessary to cause 50% mortality).

In vitro assays can also be used for screening shuffled vip3 gene libraries. Such assays typically involve the use of cultured insect cells that are susceptible to Vip3 toxins, and/or cells that express a receptor for the Vip3 toxins, either naturally or as a result of expression of a heterologous gene. Other in vitro assays can be used, for example, detection of morphological changes in cells, dyes and labels useful for detecting cell death, or detection of the release of ATPase by cells. One example of a suitable in vitro assay using cultured insect cells for Vip3 toxicity is Sf9 (*Spodoptera frugiperda*) cells. Sf9 is highly sensitive to Vip3 toxins. When Vip3 toxins are mixed with Sf9 cells, the cell membrane becomes highly permeable to small molecules. When a dye such as trypan blue is added to the cell suspension, those cells which are killed by the Vip3 toxin are stained blue. Thus, the cytotoxicity of the Vip3 toxin can be determined by image analysis.

Additional in vitro assays involve the use of receptors for the Vip3 toxins. One such receptor is disclosed in U.S. Pat. No. 6,291,156, herein incorporated by reference. The Vip3 receptor protein can be immobilized on a receiving surface, for example, without limitation, a 96-well plate or a nitrocellulose membrane, and exposed to clones comprising shuffled vip3 genes. Thus, shuffled vip3 genes that encode functional toxins can be identified on the basis of binding affinity to the Vip3 receptor. Further, the gene encoding the Vip3 receptor can be transformed into a non-Vip3 susceptible cell line, for example the Schneider 2 (S2) *Drosophila* cell line, using methods known in the art (see for example, Clem and Miller, 1194, Mol. Cel. Biol. 14:5212-522). The transformed S2 cells can then be exposed to clones comprising shuffled vip3 genes. Thus, shuffled vip3 genes that encode functional toxins can be identified on the basis of induction of cell death.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), Current Protocols in Molecular Biology, John Wiley and Sons, Inc. (1994); J. Sambrook, et al., Molecular Cloning: *A Laboratory Manual,* 3d Ed., Cold Spring Harbor, N.Y.: Cold Spring Harbor Laboratory Press (2001); and by T. J. Silhavy, M. L. Berman, and L. W. Enquist, Experiments with Gene Fusions, Cold Spring Harbor Laboratory, Cold Spring Harbor, N.Y. (1984).

Example 1

Identification of Bt Isolates that Harbor Vip3 Homologous Proteins

Three sets of PCR primers, whose sequences are based on the vip3A gene (SEQ ID NO: 5), were used in a PCR reaction to amplify fragments of possible homologous vip3 genes from *Bacillus thuringiensis* (Bt) isolates. The three primer sets used were:

```
                                        (SEQ ID NO: 12)
1F: 5'-ATGAACAAGAATAATACTAAATTAAGCACAAGAGCC-3'

                                        (SEQ ID NO: 13)
1R: 5'-CTCAACATAGAGGTAATTTTAGGTAGATATACCCG-3'
```

-continued

```
                                        (SEQ ID NO: 14)
p3: 5'-GATGATGGGGTGTATATGCCGTTAG-3'

                                        (SEQ ID NO: 15)
p4: 5'-AATAAATTGTGAAATTCCTCCGTCC-3'

                                        (SEQ ID NO: 16)
4F: 5'-AGTCAAAATGGAGATCAAGGTTGGGGAGATAAC-3'

                                        (SEQ ID NO: 17)
4R: 5'-TTACTTAATAGAGAGATCGTGGAAATGTACAATA-3'
```

Three PCR products were expected if a Bt isolate comprised a gene identical to the vip3A gene (SEQ ID NO: 4). The size of the PCR product generated by primer sets 1F/1R, p3/p4, and 4F/4R were 377 bp, 344 bp, and 419 bp, respectively. Isolates that produced only one or two PCR products, which indicated they may comprise a vip3 gene with some sequence difference to vip3A, were subjected to further sequence analysis.

Example 2

Cloning and Sequencing of PCR Products to Confirm Vip3 Homologous Sequences

Bt isolates identified in Example 1 as producing one or two PCR products were subjected to PCR again with primer set 1F/1R (SEQ ID NO: 12/SEQ ID NO: 13) as well as the following two primers:

```
                                        (SEQ ID NO: 18)
p5: 5'-AATGGAGATGAAGCTTGGGGAGAT-3'

                                        (SEQ ID NO: 19)
p6: 5'-CGTGGAAATGTACAATAGGACCACC-3'
```

The PCR products were then cloned into a pCR2.1-Topo (Invitrogen) vector and sequenced using standard art procedures.

Three Bt isolates were identified as comprising homologous vip3 genes, designated vip3C, with significant sequence differences to vip3A. These Bt isolates were designated C536, C1674 and AB727.

Example 3

PCR Cloning the Full-Length Vip3C Gene

The 3' end of the vip3C gene was obtained by PCR using total plasmid DNA isolated from Bt strain C536 or C1674 as the template. The primers used were:

```
Vip3CF4:
5'-GTTTAGAAGATTTTCAAACCATTAC-3'   (SEQ ID NO: 20)

T7:
5'-TTAATACGACTCACTATAGGG-3'       (SEQ ID NO: 21)
```

Primer T7 is a non-gene specific primer that recognizes the flanking nucleotide sequence 3' to the vip3C gene.

The PCR products were cloned and sequenced using standard art procedures. The final full-length vip3C gene was obtained by PCR using the two primers located at the 3' and 5' ends of vip3C:

```
Vip3Cc:
                                        (SEQ ID NO: 22)
5'-TTTATTTAATAGAAACGTTTTCAAATGATATATG-3'

Vip3Cn:
                                        (SEQ ID NO: 23)
5'-CACCATGAACAAGAATAATACTAAATTAAGCACAAGAG-3'
```

Two full-length vip3C genes were obtained. The vip3C gene from Bt isolate C536 was designated vip3C(a), and the vip3C gene isolated from C1674 was designated vip3C(b). Vip3C(a) and vip3C(b) differ by one nucleotide at position 2213 (See SEQ ID NO: 1), wherein vip3C(a) comprises the nucleotide "a" at position 2213, thereby encoding the amino acid Glu at position 738 of SEQ ID NO: 2, and wherein vip3C(b) comprises the nucleotide "g" at position 2213, thereby encoding a Gly at position 738 of SEQ ID NO: 2.

The vip3C(a) and the vip3C(b) genes were each cloned into pET101/D-Topo expression vectors and designated pNOV3911 and pNOV3910, deposited in *E. coli* DH5α cells, and given the accession numbers NRRL B-30552 and NRRL B-30553, respectively.

Example 4

Cosmid Cloning the Full-Length Vip3Z Gene

Total DNA was isolated from AB727 by treating freshly grown cells resuspended in 100 mM Tris pH 8, 10 mM EDTA with 2 mg/ml lysozyme for 30 minutes at 37° C. Proteinase K was added to a final concentration of 100 μg/ml in 1% SDS, 50 mM EDTA, 1M urea and incubated at 55° C. An equal volume of phenol-chloroform-isoamyl alcohol was added. The sample was gently mixed for 5 minutes and centrifuged at 3K. This was repeated twice. The aqueous phase was then mixed with 0.7 volumes isopropanol and centrifuged. The DNA pellet was washed three times with 70% ethanol and gently resuspended in 0.5× TE. 12 μg of DNA were treated with 0.3 unit of Sau3A per μg of DNA at 37° C. in a volume of 100 μl. Samples were taken at 2-min intervals for 10 minutes. Then 1/10 volume 10× TE was added and samples were heated for 30 minutes at 65° C. to inactivate the enzyme. The samples were subjected to electrophoresis to determine which fraction is in the 40-kb range and this sample was used in the ligation.

SuperCos cosmid vector (Stratagene, La Jolla, Calif.) was prepared as described by the supplier utilizing the BamHI cloning site. Prepared SuperCos at 100 ng/ml was ligated with the AB727 DNA previously digested with Sau3A at a ratio of 2:1 in a 5 μl volume overnight at 6° C. The ligation mixture was packaged using Gigapack XL III (Stratagene) as described by the supplier. Packaged phages were infected into XL-1MR *E. coli* cells (Stratagene) as described by the supplier. The cosmid library was plated on L-agar with 50 μg/ml kanamycin and incubated 16 hours at 37° C. 200 colonies were picked and grown for screening for the presence of the vip3Z gene.

The 200 cosmid clones were screened for the presence of the vip3Z gene by PCR using primer Vip3ZA: 5'-GGCATTTATGGATTTGCCACTGGTATC-3' (SEQ ID NO: 28) and primer Vip3ZB: 5'-TCCTTTGATACGCAGGTGTAATTTCAG-3' (SEQ ID NO: 29).

One cosmid clone, designated 5 g, was shown to comprise the vip3Z gene (SEQ ID NO: 8) encoding the Vip3Z protein (SEQ ID NO: 9).

Example 5

Maize Optimized Vip3C Gene Construction

A maize optimized vip3C gene was made according to the procedure disclosed in U.S. Pat. No. 5,625,136, incorporated herein by reference. In this procedure, maize preferred codons, i.e., the single codon that most frequently encodes that amino acid in maize, are used. The maize preferred codon for a particular amino acid is derived from know gene sequences from maize. Maize codon usage for 28 genes from maize plants is found in Murray et al. (1989, Nucleic Acids Res. 17:477-498).

Synthetic vip3C(a) and vip3C(b) genes were made which encode the amino acid sequence depicted in SEQ ID NO: 2. At positions 2213 and 2214 of SEQ ID NO: 3, the synthetic vip3C(a) gene comprises nucleotides “a” and “g”, respectively, encoding the amino acid Glu at position 738 of SEQ ID NO: 2, and the synthetic vip3C(b) gene comprises nucleotides “g” and “a”, respectively, encoding the amino acid Gly at position 738 of SEQ ID NO: 2. The synthetic vip3C(a) and vip3C(b) genes were separately cloned into pET101/D-Topo expression vectors and the resulting vectors designated pNOV3905, deposited in *E. coli* BL21 cells and given accession number NRRL B-30554, and pNOV3906, deposited in *E. coli* BL21 cells and given the accession number NRRL B-30555.

Example 6

Bioassay of the Vip3C Protein

Black cutworm diet (BioServ, Frenchtown, N.J.) was poured into 50 mm petri dishes. The diet was allowed to cool off and a 200 μl suspension of *E. coli* cells comprising pNOV3905, pNOV3906, pNOV3910 or pNOV3911 was pipetted onto the diet surface. The solution was uniformly spread with a bacterial loop so that the suspension covered the entire surface of the diet. The surface was allowed to dry thoroughly. First instar larvae of the lepidopteran species listed in the table below were placed on the diet with a fine tip brush. Each species was tested separately. Larval mortality, as well as the occurrence of feeding and growth inhibition, was recorded at 3 days and 5 days after larval infestation of the diet. A sample containing *E. coli* cells without an expression vector acted as the negative control. Vip3A protein can also be tested in the same bioassay for comparative purposes or for this example, Vip3C data was compared to the known activity spectrum of Vip3A.

Results are shown in Table 8. Insecticidal activity was observed five days after the plates were infested with insects. The data show that Vip3C(a) (from pNOV3911 and pNOV3905) and Vip3C(b) (from pNOV3910 and 3906) have a broader spectrum of activity than the Vip3A toxin. Tests also indicated that the Vip3C toxin is not active against the environmental beneficial insect *Danaus plexippus*.

TABLE 8

| | % Insect Mortality | | Activity Spectrum of |
|---|---|---|---|
| Insect Tested | Vip3C(a) | Vip3C(b) | Vip3A[b] |
| *Agrotis ipsilon* | 100 | 100 | + |
| *Helicoverpa zea* | 75[a] | 75[a] | + |
| *Heliothis virescens* | 80 | 50 | + |
| *Spodoptera exigua* | 100 | 100 | + |
| *Spodoptera frugiperda* | 70[a] | 70[a] | + |
| *Trichoplusia ni* | 100 | 100 | + |
| *Pectinophora gossypiella* | 50[a] | 60[a] | + |
| *Cochylis hospes* | 90 | 90 | + |
| *Homoeosoma electellum* | 40[a] | 30[a] | + |
| *Ostrinia nubilalis* | 100 | 100 | − |
| *Plutella xylostella* | 100 | 100 | − |

[a]Surviving insects were observed to have severe feeding and growth inhibition.

[b]A “+” indicates an insect species that is susceptible to Vip3A. A “−” indicates an insect species with little or no susceptibility to Vip3A.

Example 7

Creation of Transgenic Maize Plants Comprising a Vip3C Gene

Maize optimized vip3C (SEQ ID NO: 3) was chosen for transformation into maize plants. An expression cassette comprising the vip3C(a) sequence was transferred to a suitable vector for *Agrobacterium*-mediated maize transformation. For this example, an expression cassette comprised, in addition to the vip3C(a) gene, the maize ubiquitin promoter and the nos terminater which are known in the art, as well as the phosphomannose isomerase (PMI) gene for selection of transgenic lines (Negrotto et al. (2000) Plant Cell Reports 19: 798-803). The resulting vector was designated pNOV2149 (SEQ ID NO: 30).

Transformation of immature maize embryos was performed essentially as described in Negrotto et al., 2000, Plant Cell Reports 19: 798-803. For this example, all media constituents were as described in Negrotto et al., supra. However, various media constituents known in the art may be substituted.

*Agrobacterium* strain LBA4404 (pSB1) containing the plant transformation plasmid was grown on YEP (yeast extract (5 g/L), peptone (10 g/L), NaCl (5 g/L), 15 g/l agar, pH 6.8) solid medium for 2-4 days at 28° C. Approximately $0.8\times10^9$ *Agrobacterium* were suspended in LS-inf media supplemented with 100 μM As (Negrotto et al., (2000) Plant Cell Rep 19: 798-803). Bacteria were pre-induced in this medium for 30-60 minutes.

Immature embryos from the A188 maize genotype were excised from 8-12 day old ears into liquid LS-inf+100 μM As. Embryos were rinsed once with fresh infection medium. *Agrobacterium* solution was then added and embryos were vortexed for 30 seconds and allowed to settle with the bacteria for 5 minutes. The embryos were then transferred scutellum side up to LSAs medium and cultured in the dark for two to three days. Subsequently, between 20 and 25 embryos per petri plate were transferred to LSDc medium supplemented with cefotaxime (250 mg/l) and silver nitrate (1.6 mg/l) and cultured in the dark for 28° C. for 10 days.

Immature embryos, producing embryogenic callus were transferred to LSD1M0.5S medium. The cultures were selected on this medium for 6 weeks with a subculture step at 3 weeks. Surviving calli were transferred to Reg1 medium supplemented with mannose. Following culturing in the light (16 hour light/8 hour dark regiment), green tissues were then transferred to Reg2 medium without growth regulators and incubated for 1-2 weeks. Plantlets were transferred to Magenta GA-7 boxes (Magenta Corp, Chicago Ill.) containing Reg3 medium and grown in the light. After 2-3 weeks, plants were tested for the presence of the PMI genes and the vip3C(a) gene by PCR. Positive plants from the PCR assay were transferred to the greenhouse and tested for resistance to lepidopteran pests.

Example 8

Analysis of Transgenic Maize Plants

Plants were sampled as they are being transplanted from Magenta GA-7 boxes into soil. Sampling consisted of cutting two small pieces of leaf (ca. 2-4 cm long) and placing each in a small petri dish. Negative controls were either transgenic plants that were PCR negative for the vip3C(a) gene from the same experiment, or from non-transgenic plants (of a similar size to test plants) that were being grown in the phytotron.

Leaf samples from each plant were inoculated with either European corn borer (*Ostrinia nubilalis*) or fall armyworm (*Spodoptera frugiperda*) by placing 10 first instar larvae onto each leaf piece. Petri dishes were then tightly sealed.

At 3-4 days post inoculation, data were collected. The percent mortality of the larvae was calculated along with a visual damage rating of the leaf. Feeding damage was rated as high, moderate, low, or absent and given a numerical value of 3, 2, 1 or 0, respectively.

Results shown in Table 9 indicate that transgenic maize plants comprising the vip3C(a) gene and expressing the Vip3C(a) protein, are insecticidal to European corn borer (ECB) and fall armyworm (FAW).

TABLE 9

| Event | Plant No. | ECB Mortality | Damage Rating | FAW Mortality | Damage Rating |
|---|---|---|---|---|---|
| 557 | 12A | 80% | 2 | 100% | 0 |
| 557 | 20B | 100% | 1 | 100% | 0 |
| 557 | 8A | 80% | 1 | 70% | 0 |
| 557 | 11A | 100% | 2 | 100% | 0 |
| 557 | 16B | 95% | 2 | 95% | 0 |
| 557 | 18B | 90% | 2 | 100% | 0 |
| 557 | 14B | 100% | 1 | 100% | 0 |
| 556 | 1A | 100% | 1 | 100% | 0 |
| 556 | 3B | 80% | 1 | 100% | 0 |
| 556 | 4A | 95% | 1 | 100% | 0 |
| 556 | 13A | 100% | 1 | 100% | 0 |
| A188 | NEG | 0 | 10 | 0% | 10 |

Example 9

Hybrid Vip3 Toxins

Vip3C is toxic to *Ostrinia nubilalis* (European corn borer) and *Plutella xylostella* (diamond back moth), whereas homologous Vip3 toxins, for example, Vip3A(a), Vip3A(b), and Vip3A(c) are not. Vip3C and Vip3A differ primarily in the C-terminal region of their respective amino acid sequences particularly in the region from amino acid 661 to amino acid 788 of SEQ ID NO: 2. In order to demonstrate that this C-terminal region of Vip3C is the portion of the Vip3C toxin that is responsible for the activity against European corn borer and diamond back moth, a hybrid toxin comprising the C-terminal region of Vip3C, amino acid number 661 to amino acid number 788 of SEQ ID NO: 2, was joined in an amino to carboxy direction with the N-terminal region, from amino acid number 1 to amino acid number 660 of SEQ ID NO: 5, of Vip3A. This hybrid toxin was designated Vip3A-C.

A nucleic acid molecule encoding the Vip3A-C hybrid toxin, was constructed using two steps of PCR with the following primers:

```
Vip3A-N:
                                        (SEQ ID NO: 24)
5'-CACCATGAACAAGAATAATACTAAATTAAGCACAAGAG-3'

Vip3A2050:
                                        (SEQ ID NO: 25)
5'-TAAAGTTATCTCCCCAAGCTTCATCTCCA-3'

Vip3C-C1:
                                        (SEQ ID NO: 26)
5'-AATGGAGATGAAGCTTGGGGAGAT-3'

Vip3C-C2:
                                        (SEQ ID NO: 27)
5'-TTTATTTAATAGAAACGTTTTCAAATGATATATG-3'
```

In the first PCR step primers Vip3A-N (SEQ ID NO: 24) and Vip3A2050 (SEQ ID NO: 25) were used to generate an approximately 2.0 kb fragment of the 5' end of the vip3A gene, encoding the N-terminal region, and primers Vip3C-C1 (SEQ ID NO: 26) and Vip3C-C2 (SEQ ID NO: 27) were used to generate an approximately 0.4 kb fragment of the 3' end of the vip3C gene, encoding the C-terminal region. In the second PCR step, these two fragments were combined as the templates for primers Vip3A-N (SEQ ID NO: 24) and Vip3C-C2 (SEQ ID NO: 27) to generate an approximately 2.4 kb hybrid vip3A-vip3C gene, designated vip3A-C.

A hybrid vip3A-vip3C(b) gene was made, the sequence of which is set forth in SEQ ID NO: 10. The hybrid vip3A-C gene was cloned into pET101D (Novagen), and the resulting vector designated pNOV3912, and transformed into *E. coli* DH5α for expression. This *E. coli* clone, (NRRL B-30551), was tested against the insect species listed in Table 10. The Vip3C protein was used as comparative controls. Data were compared to the known activity spectrum of Vip3A.

The results shown in the Table 10 confirm that the C-terminal region of Vip3C, amino acid number 661 to amino acid number 788 of SEQ ID NO: 2, is sufficient to confer European corn borer and diamond back moth activity on the hybrid toxin.

TABLE 10

| | % Insect Mortality | | Activity Spectrum of |
|---|---|---|---|
| Insect Tested | Vip3A-C | Vip3C(b)[b] | Vip3A[c] |
| *Agrotis ipsilon* | 100 | 100 | + |
| *Helicoverpa zea* | 100 | 75[a] | + |
| *Heliothis virescens* | 60 | 50 | + |
| *Spodoptera exigua* | 80 | 100 | + |
| *Spodoptera frugiperda* | 70[a] | 70[a] | + |
| *Trichoplusia ni* | 80 | 100 | + |
| *Pectinophora gossypiella* | 80 | 60[a] | + |
| *Cochylis hospes* | 100 | 90 | + |
| *Homoeosoma electellum* | 40[a] | 30[a] | + |
| *Ostrinia nubilalis* | 100 | 100 | − |
| *Plutella xylostella* | 100 | 100 | − |

[a]Surviving insects were observed to have severe feeding and growth inhibition.

[b]Data from Example 6.

[c]A "+" indicates an insect species that is susceptible to Vip3A. A "−" indicates an insect species with little or no susceptibility to Vip3A.

Example 10

In Vitro Recombination of Vip3 Genes by DNA Shuffling

One of the vip3 genes of the present invention (SEQ ID NO: 1, 3, or 11) is amplified by PCR. The resulting DNA fragment is digested by DNaseI treatment essentially as described in Stemmer et al., *PNAS* 91: 10747-10751 (1994), and the PCR primers are removed from the reaction mixture. A PCR reaction is carried out without primers and is followed by a PCR reaction with the primers, both as described in Stemmer et al. (1994). The resulting DNA fragments are cloned into pTRC99a (Pharmacia, Cat no: 27-5007-01) and transformed into *E. coli* strain SASX38 by electroporation using the Biorad Gene Pulser and the manufacturer's conditions. The transformed bacteria are grown on medium overnight and screened for insecticidal activity.

In a similar reaction, PCR-amplified DNA fragments comprising one of the vip3 genes described herein (SEQ ID NO: 1, 3, 5, 7, 9, or 11, or mutants thereof), and PCR-amplified DNA fragments comprising at least one other of the vip3 genes described herein (or a mutant thereof) are recombined in vitro and resulting variants with improved insecticidal properties are recovered as described below.

In order to increase the diversity of the shuffled vip3 gene library, a vip3 gene or genes (called the primary genes) are shuffled using synthetic oligonucleotide shuffling. A plurality (e.g., 2, 5, 10, 20, 50, 75, or 100 or more) of oligonucleotides corresponding to at least one region of diversity are synthesized. These oligonucleotides can be shuffled directly, or can be recombined with one or more of the family of nucleic acids.

The oligonucleotide sequence can be taken from other vip3 genes called secondary genes. The secondary genes have a certain degree of homology to the primary genes. There are several ways to select parts of the secondary gene for the oligonucleotide synthesis. For example, portions of the secondary gene can be selected at random. The DNA shuffling process will select those oligonucleotides, which can be incorporated into the shuffled genes.

The selected portions can be any lengths as long as they are suitable to synthesize. The oligonucleotides can also be designed based on the homology between the primary and secondary genes. A certain degree of homology is necessary for crossover, which must occur among DNA fragments during the shuffling. At the same time, strong heterogeneity is desired for the diversity of the shuffled gene library. Furthermore, a specific portion of the secondary genes can be selected for the oligonucleotide synthesis based on the knowledge in the protein sequence and function relationship.

The present invention has disclosed that the C-terminal domain of Vip3 is in part responsible for spectrum of activity of the Vip3 toxins. When the insecticidal spectrum is modified by the current invention utilizing the DNA shuffling technology, the C-terminal region of the nucleotide sequence of the secondary genes can be selected as a target region for synthesizing oligonucleotides used in an oligonucleotide shuffling procedure.

Since the insecticidal activity of the Vip3 protein is dependent, at least in part, to the N-terminal region, the N-terminal region of the secondary genes can be selected for oligonucleotide shuffling for increased insecticidal activity.

In one aspect, the primary vip3C(a) and vip3C(b) genes are shuffled with several oligonucleotides that are synthesized based on the secondary vip3A gene sequence. Vip3C(a) and vip3C(b) are highly homologous, but vip3A is substantially different from these genes. Therefore, it is desirable to shuffle vip3A along with the vip3C(a) and vip3C(b) to increase the diversity of resulting shuffled recombinant nucleic acids. Portions of the vip3A sequence, which are substantially different from the corresponding portions of vip3C(a) and vip3C(b), are selected, and a series of 50-mer oligonucleotides that cover these portions are synthesized. These oligonucleotides are shuffled with the vip3C(a) and vip3C(b). A certain number of the clones are then selected from the shuffled gene library and examined for the diversity by restriction mapping. The diversity is contemplated to be more than normally expected from the shuffling of vip3C(a) and vip3C(b) alone.

Example 11

High-Throughput Screen for Insecticidal Activity

Shuffled vip3 gene libraries in either *E. coli* or *Bacillus thuringiensis* are screened for insecticidal activity. Colonies are picked with a Q-bot (Beckman), placed in growth media in a standard 96-well format and grown over night. Each clone is then layered onto the surface of an insect diet in 96-well format and the surface allowed to dry. Optionally, pools of transformed cells are added to each well to increase the number of clones that are tested in the initial screening round. For example, screening 100 clones per well and using 10,000 wells provides a screen of $10^6$ clones.

Several neonate larvae of a target insect, for example, *Heliothis virescens, Helicoverpa zea* or *Spodoptera frugiperda*, are added to each well. The plate is covered with an air permeable membrane that retains the larvae in the wells into which they were placed. After 5 days the wells are evaluated for amount of diet consumed and/or insect mortality. Clones in wells indicating that little or no diet is consumed and/or where high insect mortality is observed are chosen for further analysis. Several clones should be found to have enhanced activity against the target insect.

Example 12

Cosmid Cloning a Full-Length vip3C Gene

Total DNA was isolated from C1674 (NRRL B-30556) by treating freshly grown cells resuspended in 100 mM Tris pH 8, 10 mM EDTA with 2 mg/ml lysozyme for 30 minutes at 37° C. Proteinase K was added to a final concentration of 100 μg/ml in 1% SDS, 50 mM EDTA, 1M urea and incubated at 55° C. An equal volume of phenol-chloroform-isoamyl alcohol was added. The sample was gently mixed for 5 minutes and centrifuged at 3K. This was repeated twice. The aqueous phase was then mixed with 0.7 volumes isopropanol and centrifuged. The DNA pellet was washed three times with 70% ethanol and gently resuspended in 0.5× TE. 12 μg of DNA were treated with 0.3 unit of Sau3A per μg of DNA at 37° C. in a volume of 100 μl. Samples were taken at 2-min intervals for 10 minutes. Then 1/10 volume 10× TE was added and samples were heated for 30 minutes at 65° C. to inactivate the enzyme. The samples were subjected to electrophoresis to determine which fraction is in the 40-kb range and this sample was used in the ligation.

SuperCos cosmid vector (Stratagene, La Jolla, Calif.) was prepared as described by the supplier utilizing the BamHI cloning site. Prepared SuperCos at 100 ng/ml was ligated with the C1674 DNA previously digested with Sau3A at a ratio of 2:1 in a 5 μl volume overnight at 6° C. The ligation mixture was packaged using Gigapack XL III (Stratagene) as described by the supplier. Packaged phages were infected into XL-1MR *E. coli* cells (Stratagene) as described by the supplier. The cosmid library was plated on L-agar with 50 μg/ml kanamycin and incubated 16 hours at 37° C. 200 colonies were picked and grown for screening for the presence of the vip3C gene.

The 200 cosmid clones were screened for the presence of the vip3C gene by PCR using vip3C specific primers.

Two cosmid clones were shown to comprise a vip3C coding sequence. After several sequencing runs the sequence was confirmed to be the sequence set forth in SEQ ID NO: 31. This vip3C coding sequence was designated vip3C-12168 and encodes the Vip3C-12168 protein (SEQ ID NO: 32).

Example 13

Bioassay of Vip3C-12168

*E. coli* cells comprising an expression vector (pTrcHis; Invitrogen) comprising the vip3C-12168 coding sequence were tested for biological activity using the protocol described in Example 6. The insect species tested were, European corn borer (ECB), fall armyworm (FAW), black cutworm (BCW), tobacco budworm (TBW), and corn earworm (CEW). Larval mortality, as well as the occurrence of feeding and growth inhibition, was recorded at 7 days after larval infestation of the diet. A sample containing *E. coli* cells with an empty expression vector (pTrcHis) acted as the negative control. *E. coli* cells expressing the δ-endotoxin Cry1Ab and *E. coli* cells expressing Vip3A protein were also tested in the same bioassay for comparison of spectrum of activity.

Results are shown in Table 11. The data show that Vip3C-12168 has the same spectrum of activity as a combination of Cry1Ab and Vip3A.

TABLE 11

| | % Mortality | | | | |
|---|---|---|---|---|---|
| Treatment | ECB | FAW | BCW | TBW | CEW |
| Cry1Ab | 100 | 0 | 10 | 0[a] | 8 |
| Vip3A | 0 | 100 | 100 | 83[b] | 100 |
| Vip3C-12168 | 100 | 100 | 100 | 92[b] | 100 |
| PTrcHis (empty vector) | 0 | 0 | 10 | 0 | 8 |

[a]Growth inhibition;
[b]Feeding inhibition

Example 14

Maize Optimized Vip3C-12168

A maize optimized vip3C-12168 coding sequence was designed according to the procedure described in Example 5. The nucleotide sequence of the maize optimized vip3C-12168 coding sequence is shown in SEQ ID NO: 33.

All publications and patent applications mentioned in this specification are indicative of the level of skill of those skilled in the art that this invention pertains. All publications and patent applications are herein incorporated by reference to the same extent as if each individual publication or patent application was specifically and individually indicated to be incorporated by reference.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A chimeric gene comprising a heterologous promoter sequence operatively linked to an isolated nucleic acid molecule comprising a nucleotide sequence that encodes a Vip3 toxin that is active against at least European corn borer, wherein the nucleotide sequence (a) has at least 99% sequence identity with SEQ ID NO: 1; or (b) encodes an amino acid sequence that has at least 95% identity with SEQ ID NO: 2; or (c) is a synthetic sequence of (a) or (b) that has been designed for expression in a plant.

2. The chimeric gene of claim 1, wherein said molecule comprises SEQ ID NO: 1 or SEQ ID NO: 10 or SEQ ID NO: 31.

3. An isolated nucleic acid molecule comprising a nucleotide sequence that encodes a Vip3 toxin that is active against at least European corn borer, wherein the nucleotide sequence is a synthetic sequence that has been designed for expression in a plant, and wherein said nucleotide sequence (a) has at least 99% sequence identity with SEQ ID NO: 1; or (b) encodes an amino acid sequence that has at least 95% identity with SEQ ID NO: 2.

4. The isolated nucleic acid molecule of claim 3, wherein said synthetic sequence has an increased GC content relative to the GC content of SEQ ID NO: 1 or SEQ ID NO: 10 or SEQ ID NO: 31.

5. The isolated nucleic acid molecule of claim 3, wherein said plant is a maize plant.

6. The isolated nucleic acid molecule of claim 3, wherein said synthetic sequence comprises SEQ ID NO: 3 or SEQ ID NO: 33.

7. The chimeric gene of claim 1 comprising nucleotides 1981-2367 of SEQ ID NO: 1 or SEQ ID NO: 3.

8. The chimeric gene of claim 1, wherein said molecule encodes a polypeptide comprising the amino acid sequence of SEQ ID NO: 2 or SEQ ID NO: 11 or SEQ ID NO: 32.

9. The chimeric gene of claim 1, wherein said amino acid sequence comprises amino acids 681-788 of SEQ ID NO: 2.

10. The chimeric gene of claim 1, wherein said Vip3 toxin is active against an insect selected from the group consisting of: *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth).

11. A recombinant vector comprising the chimeric gene of claim 1.

12. A transgenic host cell comprising the chimeric gene of claim 1.

13. The transgenic host cell according to claim 12, which is a bacterial or a plant cell.

14. A transgenic plant comprising the transgenic plant cell of claim 13.

15. The transgenic plant according to claim 14, wherein said plant is selected from the group consisting of sorghum, wheat, sunflower, tomato, cole crops, cotton, rice, soybean, sugar beet, sugarcane, tobacco, barley, oilseed rape and maize.

16. The transgenic plant according to claim 15, wherein said plant is a maize plant.

17. Transgenic seed from the transgenic plant of claim 15, wherein the seed comprises the chimeric gene.

18. Transgenic seed from the maize plant of claim 16, wherein the seed comprises the chimeric gene.

19. A method of producing a Vip3 toxin that is active against insects, said method comprising:

(a) obtaining the transgenic host cell according to claim 12;

(b) culturing said transgenic host cell under conditions that permit production of the Vip3 toxin; and (c) recovering said Vip3 toxin.

20. A method of producing an insect-resistant transgenic plant, said method comprising introducing the chimeric gene of claim 1 into a plant cell; and regenerating a transformed plant from said plant cell, wherein said transformed plant is resistant to insects.

21. The method of claim 20, wherein said insects are lepidopteran insects.

22. The method of claim 21, wherein said lepidopteran insects are selected from the group consisting of: *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth).

23. A recombinant vector comprising the isolated nucleic acid molecule of claim 3.

24. A transgenic plant cell comprising the isolated nucleic acid molecule of claim 3.

25. A transgenic plant comprising the transgenic plant cell of claim 24.

26. The transgenic plant according to claim 25, wherein said plant is a maize plant.

27. Transgenic seed from the transgenic plant of claim 26, wherein the seed comprises the nucleic acid.

28. A method of producing an insect-resistant transgenic plant, said method comprising introducing the isolated nucleic acid molecule of claim 3 into a plant cell; and regenerating a transformed plant from said plant cell, wherein said transformed plant is resistant to insects.

29. The method of claim 28, wherein said insects are lepidopteran insects.

* * * * *